United States Patent [19]

Cullen et al.

[11] Patent Number: 5,712,281

[45] Date of Patent: *Jan. 27, 1998

[54] INSECTICIDAL SUBSTITUTED-2,4-DIAMINO-5,6,7,8-TETRAHYDROQUINAZOLINES

[75] Inventors: Thomas G. Cullen, Milltown; Robert N. Henrie, II, East Windsor; Clinton J. Peake, Trenton, all of N.J.; Brian D. Bennett, Morrisville, Pa.

[73] Assignee: FMC Corporation, Philadelphia, Pa.

[*] Notice: The term of this patent shall not extend beyond the expiration date of Pat. No. 5,536,725.

[21] Appl. No.: 445,201

[22] Filed: May 23, 1995

Related U.S. Application Data

[62] Division of Ser. No. 319,504, Oct. 6, 1994, Pat. No. 5,536,725, which is a continuation of Ser. No. 111,802, Aug. 25, 1993, abandoned.

[51] Int. Cl.$^6$ .................................................. A01N 43/54
[52] U.S. Cl. ........................................ 514/259; 514/260
[58] Field of Search ................................ 514/259, 260; 544/229, 253, 291

[56] References Cited

U.S. PATENT DOCUMENTS

| | | | |
|---|---|---|---|
| 3,299,068 | 1/1967 | Chinn | 544/253 |
| 3,357,981 | 12/1967 | Ursprung et al. | 514/259 |
| 3,483,205 | 12/1969 | Carney | 544/253 |
| 3,915,976 | 10/1975 | Salmond | 544/253 |
| 4,435,402 | 3/1984 | Tsuji et al. | 424/251 |
| 4,451,466 | 5/1984 | Horne et al. | 514/241 |
| 4,845,097 | 7/1989 | Matsumoto et al. | 514/234.2 |
| 4,895,849 | 1/1990 | Yoshioka et al. | 514/241 |
| 4,985,426 | 1/1991 | Yoshioka et al. | 514/241 |
| 5,073,548 | 12/1991 | Obata et al. | 514/259 |
| 5,536,725 | 7/1996 | Cullen et al. | 514/259 |

FOREIGN PATENT DOCUMENTS

| | | |
|---|---|---|
| 831938 | of 1976 | Belgium . |
| 424125 | of 1991 | European Pat. Off. . |
| 4029650 | of 1992 | Germany . |
| 7206067 | of 1972 | Netherlands . |
| 5921065 | of 1965 | WIPO . |

OTHER PUBLICATIONS

Kinnamon et al. I, Exp. Parasitol., 1980, 49(2) 277–80.

Kinnamon et al. II, J. Med. Chem., 1977 20(6) 741–744.

Blaney, et al. "Structure–Activity Relationships of Dihydrofolate Inhibitors", Chem. Reviews (A.C.S), vol. 84, No. 4 (1984) pp. 333–407.

DeGraw et al, J. Org. Chem. 24, 1632–40 (1959)—"Potential Anticancer Agents".

DeGraw et al, CA 57: 12486 (J. or Chem., 27, 576–80 (1962) "Potential Anticancer Agents".

Hiroak et al, CA 112: 217539y (1990).

Ashton et al, CA 79;142777p (1973).

*Primary Examiner*—José G. Dees
*Assistant Examiner*—Mary C. Cebulak
*Attorney, Agent, or Firm*—Stanford M. Back; Robert M. Kennedy

[57] ABSTRACT

There is provided an insecticidal composition comprising, in admixture with an agriculturally acceptable carrier, an insecticidally effective amount of a tetrahydroquinazoline compound of the formula (I)

wherein R, $R^1$, $R^2$, $R^3$, $R^5$, $R^6$, $R^7$, $R^8$, and $R^9$ are as defined herein, and methods of using the same. Certain novel substituted-phenyl tetrahydroquinazoline compounds per se are also identified.

3 Claims, No Drawings

INSECTICIDAL SUBSTITUTED-2,4-DIAMINO-5,6,7,8-TETRAHYDROQUINAZOLINES

This application is a divisional of application Ser. No. 08/319,504, filed Oct. 6, 1994, now U.S. Pat. No. 5,536,725, which in turn is a continuation of application Ser. No. 08/111,802, filed Aug. 25, 1993, now abandoned.

BACKGROUND OF THE INVENTION

This invention relates to tetrahydroquinazoline compounds and compositions containing the same which are useful for controlling insects in agricultural crops. Still more particularly, this invention relates to certain 2,4-diamino-5,6,7,8-tetrahydroquinazoline compounds and compositions, and their use as insecticides against a variety of insects, including larvae, such as the tobacco budworm. Numerous of these diaminotetrahydroquinazoline compounds employed herein, and their preparation, have been described in the literature for use in a variety of fields, but not as insecticides.

SUMMARY OF THE INVENTION

In accordance with the present invention it has been found that substituted-2,4-diamino-5,6,7,8-tetrahydroquinazolines (hereinafter "tetrahydroquinazolines"), and agriculturally acceptable salts thereof, when present in insecticidally effective amounts, and with a suitable agricultural carrier, are useful as active ingredients in the insecticidal compositions and methods of this invention. These tetrahydroquinazolines may be represented by the following structure:

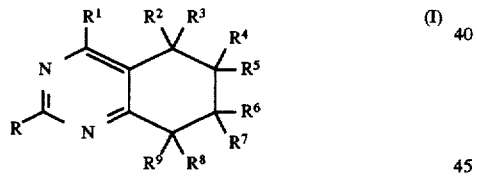

(I)

wherein

R is amino, lower alkylthio (e.g., —SCH$_3$), lower alkylsulfinyl (e.g., —S(O)CH$_3$), or —NR$^{11}$R$^{12}$, where R$^{11}$ is hydrogen or lower alkyl (e.g., —CH$_3$), and R$^{12}$ is lower alkyl (e.g., —CH$_3$); or R$^{11}$ and R$^{12}$ taken together are —(CH$_2$)$_4$—, —(CH$_2$)$_5$—, or —(CH$_2$)$_2$—O—(CH$_2$)$_2$—, forming a ring to provide the corresponding pyrrolidin-1-yl, piperidin-1-yl, and morpholin-4-yl heterocyclic ring systems, respectively;

R$^1$ is amino;

R$^2$ and R$^6$ are hydrogen or lower alkyl (e.g., —CH$_3$);

R$^3$, R$^5$, R$^7$, R$^8$, and R$^9$ are hydrogen;

R$^4$ is hydrogen, straight or branched chain alkyl (e.g., —CH$_3$, —C$_3$H$_7$, —C$_9$H$_{19}$, —CH(CH$_3$)C$_3$H$_7$), or —C(CH$_3$)$_3$), or cycloalkyl (e.g., cyclohexyl); or R$^4$ and R$^5$, taken together are —OCH$_2$CH$_2$O—, forming a 1,4-dioxaspiro ring system; or, R$^4$ is —(n)$_m$—R$^{10}$, where m is 0; and R$^{10}$ is

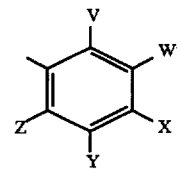

wherein

V, W, X, Y and Z are hydrogen, halogen (e.g., Cl or F), lower alkyl (e.g., —CH$_3$), lower haloalkyl (e.g., —CF$_3$), cyano, lower alkoxycarbonyl (e.g., —CO$_2$CH$_3$), aryl (e.g., phenyl), aryl (e.g., phenyl) substituted with halogen (e.g., F) or lower haloalkyl (e.g., —CF$_3$), or aryloxy (e.g., phenoxy); or, V and W, or W and X taken together are —OC(CH$_3$)$_2$CH$_2$—, —CH$_2$C(CH$_3$)$_2$O—, —OCF$_2$CF$_2$—, —CF$_2$CF$_2$O—, —CH=CHCH=CH—, —OC(CH$_3$)$_2$C(=O)—, —C(=O)C(CH$_3$)$_2$O—, or —OCF$_2$O—, forming a fused ring, to provide the corresponding 2,3-dihydro-2,2-dimethylbenzofuran-7-yl, 2,3-dihydro-2,2-dimethylbenzofuran-6-yl, 2,3-dihydro-2,2-dimethylbenzofuran-4-yl, 2,3-dihydro-2,2-dimethylbenzofuran-5-yl, 2,2,3,3-tetrafluorobenzofuran-7-yl, 2,2,3,3-tetrafluorobenzofuran-6-yl, 2,2,3,3-tetrafluorobenzofuran-4-yl, 2,2,3,3-tetrafluorobenzofuran-5-yl, naphth-1-yl, naphth-2-yl, 2,3-dihydro-2,2-dimethyl-3-benzofuranon-7-yl, 2,3-dihydro-2,2-dimethyl-3-benzofuranon-6-yl, 2,3-dihydro-2,2-dimethyl-3-benzofuranon-4-yl, 2,3-dihydro-2,2-dimethyl-3-benzofuranon-5-yl, 2,2-difluoro-1,3-benzodioxol-4-yl and 2,2-difluoro-1,3-benzodioxol-5-yl ring systems, respectively; or, R$^4$ is —(n)$_m$—R$^{10}$, where m is 1; n is a bridging atom or group selected from oxygen, sulphur, sulfinyl, sulfonyl, carbonyl, straight or branched chain lower alkylene (e.g., —CH$_2$—, —C(CH$_3$)$_2$—), lower haloalkenylene (e.g., —C(Cl)=CH—), lower oxyalkylene (e.g., —OCH$_2$—), iminooxy (=NO—), iminooxy lower alkylene (e.g., =NOCH$_2$—), and lower dialkylsilyl (e.g., —Si(CH$_3$)$_2$—).

The preferred compounds of the present invention are those of Formula I wherein

R and R$^1$ are amino;

R$^2$, R$^3$, R$^5$, R$^6$, R$^7$, R$^8$, and R$^9$ are hydrogen; and

R$^4$ is alkyl (e.g., —C(CH$_3$)$_3$ i.e. Compound 4), cycloalkyl (e.g., cyclohexyl i.e. Compound 6), or —(n)$_m$—R$^{10}$, where m is 1; n is the bridging group straight or branched chain lower alkylene (e.g., —CH$_2$—, —C(CH$_3$)$_2$—) or sulfonyl; and R$^{10}$ is

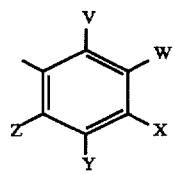

wherein

Z is hydrogen; and V, W, X, and Y are hydrogen, halogen (e.g., Cl), lower haloalkyl (e.g., —CF$_3$); (Compounds 52–55, 59, 65, 66, 68, 95, 97, 102, 109, and 111); or, V and W, or W and X, taken together are —OC $(CH_3)_2CH_2$—, —$CH_2C(CH_3)_2O$— or —CH=CHCH=CH—, forming a fused ring, to provide the corresponding 2,3-dihydro-2,2-dimethylbenzofuran-7-yl, 2,3-dihydro-2,2-dimethylbenzofuran-4-yl, and naphth-2-yl ring systems, respectively (Compounds 77, 79 and 269).

Compounds of the present invention that are particularly preferred are those of Formula I wherein R, $R^1$, $R^2$, $R^3$, $R^5$, $R^6$, $R^7$, $R^8$, and $R^9$ are as defined in Formula I, and $R^4$ is 1,1-dimethylethyl (Compound 4), cyclohexyl (Compound 6), or —$(n)_m$—$R^{10}$, where m is 1; n is —$CH_2$—, and $R^{10}$ is

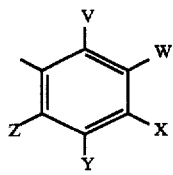

wherein

V is chloro or trifluoromethyl, and W, X and Y are hydrogen, (Compounds 53 and 65) or W and Y are chloro (Compound 59), or trifluoromethyl (Compound 68), and V and X are hydrogen; or, $R^4$ is —$(n)_m$—$R^{10}$, where m is 1; n is —$C(CH_3)_2$—, and $R^{10}$ is

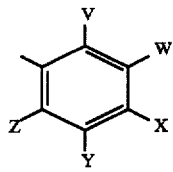

wherein

W is chloro or trifluoromethyl, and V, X, and Y are hydrogen (Compounds 97 and 109); or W and Y are chloro, and V and X are hydrogen (Compound 102); or, $R^4$ is —$(n)_m$—$R^{10}$, where m is 1; n is —$S(O)_2$—, and $R^{10}$ is

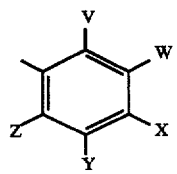

wherein

W and X, taken together are —CH=CHCH=CH—, forming a naphth-2-yl ring system (Compound 269).

In a further embodiment, this invention is also directed to certain novel substituted phenyl tetrahydroquinazolines per se falling within the scope of Formula I above. These compounds, as illustrated by Compounds 10–51, 53–148, and 150–269 of Table I below, include the following novel tetrahydroquinazolines, which may be prepared by methods that are provided in detail in the preparative Examples 2, 3, and 5–9:

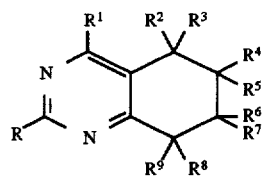

wherein

R and $R^1$ are amino;

$R^2$ and $R^6$ are hydrogen or lower alkyl (e.g., —$CH_3$);

$R^3$, $R^5$, $R^7$, $R^8$, and $R^9$ are hydrogen; and $R^4$ is —$(n)_m$—$R^{10}$, where m is 0; and $R^{10}$ is

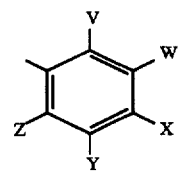

wherein

V, W, X, Y and Z are selected from halogen (e.g., Cl or F), lower alkyl (e.g., —$CH_3$), lower haloalkyl (e.g., —$CF_3$), cyano, lower alkoxycarbonyl (e.g., —$CO_2CH_3$), aryl (e.g., phenyl), aryl (e.g., phenyl) substituted with halogen (e.g., F) or lower haloalkyl (e.g., —$CF_3$), or aryloxy (e.g., phenoxy); or, V and W, or W and X, taken together, are —$OC(CH_3)_2CH_2$—, —$CH_2C(CH_3)_2O$—, —$OCF_2CF_2$—, —$CF_2CF_2O$—, —CH=CHCH=CH—, —$OC(CH_3)_2C(=O)$—, —$C(=O)C(CH_3)_2O$—, or —$OCF_2O$—, forming a fused ring, to provide the corresponding 2,3-dihydro-2,2-dimethylbenzofuran-7-yl, 2,3-dihydro-2,2-dimethylbenzofuran-6-yl, 2,3-dihydro-2,2-dimethylbenzofuran-4-yl, 2,3-dihydro-2,2-dimethylbenzofuran-5-yl, 2,2,3,3-tetrafluorobenzofuran-7-yl, 2,2,3,3-tetrafluorobenzofuran-6-yl, 2,2,3,3-tetrafluorobenzofuran-4-yl, 2,2,3,3-tetrafluorobenzofuran-5-yl, naphth-1-yl, naphth-2-yl, 2,3-dihydro-2,2-dimethyl-3-benzofuranon-7-yl, 2,3-dihydro-2,2-dimethyl-3-benzofuranon-6-yl, 2,3-dihydro-2,2-dimethyl-3-benzofuranon-4-yl, 2,3-dihydro-2,2-dimethyl-3-benzofuranon-5-yl, 2,2-difluoro-1,3-benzodioxol-4-yl, and 2,2-difluoro-1,3-benzodioxol-5-yl ring systems, respectively; or, $R^4$ is —$(n)_m$—$R^{10}$, where m is 1; and n is a bridging atom or group selected from oxygen, sulphur, sulfinyl, sulfonyl, carbonyl, straight or branched chain lower alkylene (e.g., —$CH_2$—, —$C(CH_3)_2$—), lower haloalkenylene (e.g., —C(Cl)=CH—), lower oxyalkylene (e.g., —$OCH_2$—), iminooxy (=NO—), iminooxy lower alkylene (e.g., =$NOCH_2$—), and lower dialkylsilyl (e.g., —$Si(CH_3)_2$—);

with the proviso that when m is 0; or when m is 1 and the bridging atom or group is oxygen or lower alkylene (e.g., —$CH_2$—), and $R^{10}$ is

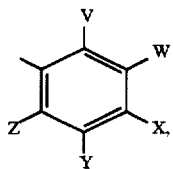

then at least one of V, W, X, Y, and Z is other than hydrogen.

Each of the above novel substituted tetrahydroquinazoline compounds per se falling within the scope of Formula (I) are preferred because of their high insecticidal activity, and may be used in controlling insects by applying to the locus where control is desired an insecticidal amount of these compounds admixed in a suitable agricultural carrier. When thus applied to insect-infected crops such as cotton, vegetables, fruits or other crops, these compounds are highly effective against an array of insects, particularly those shown in the tables below.

For the purposes of this invention, as regards the above substituent groups, the following definitions apply:

The term alkyl includes straight or branched chained alkyl of 1 to 14 carbon atoms, preferably lower straight or branched alkyl of 1 to 6 carbon atoms; while halogen includes chlorine, bromine, fluorine and iodine atoms. The term haloalkyl includes straight or branched chain alkyl of 1 to 14 carbon atoms, preferably lower straight or branched alkyl of 1 to 6 carbon atoms, wherein one or more hydrogen atoms have been replaced with halogen atoms, as, for example, trifluoromethyl. The terms alkylthio and alkylsulfinyl include straight or branched chain alkyl of 1 to 14 carbon atoms, preferably lower straight or branched alkyl of 1 to 6 carbon atoms, e.g., methylthio and methylsulfinyl, respectively. The terms lower alkoxy, lower dialkylamino, and lower alkoxycarbonyl include those moieties having 1 to 6 carbon atoms, e.g., ethoxy, N,N-dimethylamino, and methoxycarbonyl, respectively.

The terms aryl and substituted aryl include phenyl and naphthyl, preferably phenyl or substituted phenyl. The term substituted aryl includes those groups substituted with one or more alkyl, halo, haloalkyl, or lower alkoxycarbonyl groups, or the like.

The term aryloxy includes phenoxy, naphthoxy, substituted phenoxy and substituted naphthoxy, preferably phenoxy and substituted phenoxy. The term substituted aryloxy includes those groups substituted with one or more alkyl, halo, haloalkyl, or lower alkoxycarbonyl groups, or the like.

The terms lower alkylene and lower dialkyl in the bridging groups selected from straight or branched chain lower alkylene (e.g., —CH$_2$—, —C(CH$_3$)$_2$—), lower oxyalkylene (e.g., —OCH$_2$—), iminooxy lower alkylene (e.g., =NOCH$_2$—), and lower dialkylsilyl (e.g., —Si(CH$_3$)$_2$—) include straight or branched chain alkylene or alkyl of 1 to 6 carbon atoms, preferably lower straight or branched alkyl of 1 to 4 carbon atoms.

In addition, the bridging group lower haloalkenylene (e.g., —C(Cl)=CH—) includes ethenyl substituted with either chlorine or fluorine atoms.

DETAILED DESCRIPTION OF THE INVENTION

Synthesis of The Compounds

The compounds employed as insecticides in accordance with this invention are generally known to those skilled in the art, including commercial preparations thereof, or may readily be prepared from these compounds by known methods. These and other methods are described in further detail in the description and examples below.

Thus, in general, these compounds may be prepared by the reaction of a 4-substituted cyclohexanone with cyanoguanidine in a solvent, such as 2-(2-ethoxyethoxy)ethanol. The reaction mixture, which when heated to about 160° C., will afford the corresponding 2,4-diamino-6-substituted-5,6,7,8-tetrahydroquinazoline. Examples 1 and 4 provide a detailed description of how this reaction is conducted.

Cyanoguanidine, and many 4-substituted-cyclohexanones, used in the preparation of the targeted 2,4-diamino-6-substituted-5,6,7,8-tetrahydroquinazolines of this invention are available from commercial sources. However, depending on what the bridging atom or group n is when R$^4$ is —(n)$_m$—R$^{10}$ and m is 1, a number of other 4-substituted-cyclohexanones must be prepared in the laboratory. The routes used to prepare the 4-substituted-cyclohexanones are also known to one skilled in the art.

For example, when n is the bridging group —CH$_2$—, an appropriately substituted or unsubstituted phenylmethyl bromide, for example, 2-chlorophenylmethyl bromide, is reacted with triphenylphosphine in toluene, affording the corresponding phenylmethyltriphenylphosphonium bromide. The so-prepared phosphonium bromide is then treated with n-butyllithium, and reacted with 1,4-cyclohexanedione mono-ethylene ketal, yielding the appropriate 8-phenylmethylene-1,4-dioxaspiro[4.5]-decane. The 8-phenylmethylene-1,4-dioxaspiro[4.5]-decane is in turn reduced with hydrogen gas in the presence of 10% palladium on charcoal, giving the corresponding 8-phenylmethyl-1,4-dioxaspiro[4.5]-decane. The 1,4-dioxaspiro functional group is then cleaved from the so-prepared molecule with acetic acid and water, affording the corresponding 4-phenylmethylcyclohexanone. The 4-phenylmethylcyclohexanone is then reacted with cyanoguanidine, as previously described, yielding the targeted 2,4-diamino-6-phenylmethyl-5,6,7,8-tetrahydroquinazoline. Example 2 provides a detailed description of how this reaction is conducted.

The chemistry described above is applicable to the preparation of more complex 2,4-diamino-6-substituted-5,6,7,8-tetrahydroquinazolines. For example, 2,3-dihydro-2,2-dimethylbenzofuran-7-ylmethyl bromide and 2,2,3,3-tetrafluoro-2,3-dihydrobenzofuran-7-ylmethyl bromide are reacted in the same manner as shown above, yielding the corresponding targeted 2,4-diamino-6-(2,3-dihydro-2,2-dimethylbenzofuran-7-ylmethyl)-5,6,7,8-tetrahydroquinazoline and 2,4-diamino-6-(2,2,3,3-tetrafluoro-2,3-dihydrobenzofuran-7-ylmethyl)-5,6,7,8-tetrahydroquinazoline, respectively. Examples 5 and 6 provide a detailed description of how these reactions are conducted.

In an alternate method, when n is the bridging group —CH$_2$—, the 8-phenylmethylene-1,4-dioxaspiro[4.5] decane is treated with acetic acid and water as previously described, yielding the corresponding 4-phenylmethylenecyclohexanone. The cyclohexanone is then reduced with hydrogen gas in the presence of 10% palladium on charcoal (Degussa type), yielding the corresponding 4-phenylmethylcyclohexanol, which is in turn treated with sodium dichromate and sulfudc acid in water, affording the 4-phenylmethylcyclohexanone. The 4-phenylmethylcyclohexanone is then reacted with cyanoguanidine, as previously described, yielding the targeted 2,4-diamino-6-phenylmethyl-5,6,7,8-tetrahydroquinazoline. Example 3 provides a detailed description of how this reaction is conducted.

When n is the bridging group —C(CH$_3$)$_2$—, an appropriately substituted or unsubstituted phenyl methyl ketone, for example, methyl (3-chlorophenyl) ketone, is prepared by the reaction of methylmagnesium bromide and an appropriate benzonitrile in tetrahydrofuran. The ketone is in turn treated with methylmagnesiun bromide in tetrahydrofuran, yielding the corresponding 2-phenylpropan-2-ol, which is then converted to the 2-bromo-2-phenylpropane by the treatment of the alcohol with lithium bromide and trimethylsilyl chloride in acetonitrile. The Grignard reagent of the 2-bromo-2-phenylpropane is then prepared and reacted with 1,4-cyclohexanedione mono-ethylene ketal in tetrahydrofuran, yielding the corresponding 1-(2-phenylpropan-2-yl)-1-cyclohexen-4-one. The so-prepared cyclohexenone is reduced with hydrogen gas in the presence of 10% palladium on charcoal, yielding the 4-(2-phenylpropan-2-yl)cyclohexanone, which is in turn reacted with cyanoguanidine, as previously described, yielding the targeted 2,4-diamino-6-(2-phenylpropan-2-yl)-5,6,7,8-tetrahydroquinazoline. Example 7 provides a detailed description of how this reaction is conducted.

When n is the bridging group —C(Cl)=CH—, 1,4-cyclohexanedione mono-ethylene ketal is reduced with sodium borohydride in ethanol, yielding the corresponding 1,4-dioxaspiro[4.5]decan-8-ol. The so-prepared alcohol is then treated with methanesulfonyl chloride under basic conditions in methylene chloride, affording 8-methylsulfonyloxy-1,4-dioxaspiro[4.5]decane, which is in turn treated with sodium hydride in tetrahydrofuran, and then is reacted with trimethylsilylacetylene, yielding 8-(trimethylsilylethynyl)-1,4-dioxaspiro[4.5]decane. This compound is then treated with sodium carbonate in methanol to unprotect the ethynyl moiety, affording 8-ethynyl-1,4-dioxaspiro[4.5]decane. The so-prepared ethynyl compound is reacted with an appropriately substituted or unsubstituted phenyl iodide, for example, 3,5-di(trifluoromethyl)phenyl iodide, under basic conditions in the presence of bis(triphenylphosphine)palladium(II) chloride and copper(I) iodide in acetonitrile, and then is treated with 1N hydrochloric acid, yielding the corresponding 4-(phenylethynyl)cyclohexanone. The cyclohexanone is then reacted with cyanoguanidine, as previously described, affording the 2,4-diamino-6-phenylethynyl-5,6,7,8-tetrahydroquinazoline. Chlorination of the 6-phenylethynyl-5,6,7,8-tetrahydroquinazoline, using the methods of J. Cousseau (JCS Faraday II, 1973, 1821, and JCS Perkin I, 1977, 1797), affords the targeted 2,4-diamino-6-[1-chloro-2-phenylethenyl]-5,6,7,8-tetrahydroquinazoline. Example 8 provides a detailed description of how this reaction is conducted.

When the bridging group is carbonyl, the Grignard reagent of 8-bromo-1,4-dioxaspiro[4.5]decane is first prepared. The precursor 8-bromo-1,4-dioxaspiro[4.5]decane is prepared by the method of E. L Snyder (JOC, 36, 403 (1971)). The Grignard reagent is in turn reacted with an appropriately substituted or unsubstituted benzaldehyde, for example, 3-trifluoromethylbenzaldehyde and then treated with aqueous ammonium chloride, yielding [(1,4-dioxaspiro [4.5]decan-8-yl)(phenyl)]methanol. The so-prepared alcohol is treated with sodium hydride in toluene, and then is reacted with phenylmethyl bromide, yielding phenylmethyl [(1,4-dioxaspiro[4.5]decan-8-yl)(phenyl)]methyl ether. The 1,4-dioxaspiro functional group is then cleaved from the so-prepared molecule with acetic acid and water, as previously described, affording the corresponding phenylmethyl [(cyclohexanon-4-yl)(phenyl)]methyl ether. The ether is then reacted with cyanoguanidine, as previously described, yielding the appropriate 2,4-diamino-6-[(phenylmethoxy)(phenyl)methyl]-5,6,7,8-tetrahydroquinazoline. The tetrahydroquinazoline is then cleaved with hydrogen gas in the presence of 5% palladium on charcoal, yielding the corresponding [(2,4-diamino-5,6,7,8-tetrahydroquinazolin-6-yl)(phenyl)]methanol. Using the method of D. Swern (Tetrahedron, 34, 1651–1660 (1978)), the methanol is oxidized with oxalyl chloride and dimethyl sulfoxide in methylene chloride, yielding the targeted 2,4-diamino-6-phenylcarbonyl-5,6,7,8-tetrahydroquinazoline. Example 9 provides a detailed description of how this reaction is conducted.

When the bridging atom n is oxygen, an appropriately substituted or unsubstituted phenol, for example, 3-trifluoromethylphenol, is treated with sodium hydride in toluene and reacted with 8-methylsulfonyloxy-1,4-dioxaspiro[4.5]decane (the preparation of which was previously described), yielding the corresponding 8-phenoxy-1,4-dioxaspiro[4.5]decane. The 1,4-dioxaspiro functional group is then cleaved from the so-prepared molecule with acetic acid and water, affording the corresponding 4-phenoxycyclohexanone, which is in turn reacted with cyanoguanidine, yielding the targeted 2,4-diamino-6-phenoxy-5,6,7,8-tetrahydroquinazoline. Example 10 provides a detailed description of how this reaction is conducted.

When the bridging group n is —OCH$_2$—, 1,4-dioxaspiro [4.5]decan-8-ol (the preparation of which was previously described) is treated with sodium hydride and reacted with an appropriately substituted or unsubstituted phenylmethyl bromide, for example, 3-trifluoromethylphenylmethyl bromide, affording the corresponding 8-phenylmethoxy-1,4-dioxaspiro[4.5]decane. The 1,4-dioxaspiro functional group is then cleaved from the so-prepared molecule with acetic acid and water, affording the corresponding 4-phenylmethoxycyclohexanone, which is in turn reacted with cyanoguanidine, yielding the targeted 2,4-diamino-6-phenylmethoxy-5,6,7,8-tetrahydroquinazoline. Example 11 provides a detailed description of how this reaction is conducted.

When the bridging group n is =NO—, 2,4-diamino-5,6,7,8-tetrahydroquinazoline 6-ethylene ketal is prepared from 1,4-cyclohexanedione mono-ethylene ketal and cyanoguanidine, as previously described. The 2,4-diamino moieties are then protected by the reaction of 2,4-diamino-5,6,7,8-tetrahydroquinazoline 6-ethylene ketal with pivalic anhydride in the presence of 4-dimethylaminopyridine, yielding 2,4-di[(1,1-dimethylethyl)carbonylamino]-5,6,7,8-tetrahydroquinazoline 6-ethylene ketal. The 6-ethylene ketal functional group is then cleaved from the so-prepared molecule with acetic acid and water, affording the corresponding 2,4-di[(1,1-dimethylethyl)carbonylamino]-5,6,7,8-tetrahydro-6-quinazolinone. A second intermediate, an O-(phenyl)hydroxylamine, is prepared by the reaction of an appropriately substituted or unsubstituted phenol, for example, 3,5-dichlorophenol, with O-(2,4-dinitrophenyl) hydroxylamine [prepared by the method of T. Sheradsky et al (Tetrahedron, 28, 3833 (1972)). The so-prepared O-(phenyl)hydroxylamine, for example, O-(3,5-dichlorophenyl)hydroxylamine, is then reacted with the 2,4-di[(1,1-dimethylethyl)carbonylamino]-5,6,7,8-tetrahydro-6-quinazolinone in ethanol, yielding the corresponding 2,4-di[(1,1-dimethylethyl)carbonylamino]-6-phenoxyimino-5,6,7,8-tetrahydroquinazoline. Treatment of the 2,4-di[(1,1-dimethylethyl)carbonylamino]-6-phenoxyimino-5,6,7,8-tetrahydroquinazoline with methanolic hydrochloric acid yields the targeted 2,4-diamino-6-phenoxyimino-5,6,7,8-tetrahydroquinazoline. Example 12 provides a detailed description of how this reaction is conducted.

When the bridging group n is =NOCH$_2$—, an appropriately substituted or unsubstituted phenylmethyl chloride, for example, 3-trifluoromethylphenylmethyl chloride, is reacted under basic conditions with N-hydroxyphthalimide in dimethyl sulfoxide, yielding the corresponding N-(phenylmethoxy)phthalimide. The so-prepared phthalimide is in turn reacted with hydrazine monohydrate in ethanol, affording an O-(phenylmethyl)hydroxylamine, for example, O-(3-trifluorophenylmethyl)hydroxylamine. The O-(phenylmethyl)hydroxylamine is then reacted with 2,4-di [(1,1-dimethylethyl)carbonylamino]-5,6,7,8-tetrahydro-6-quinazolinone, as described above, yielding the targeted 2,4-diamino-6-phenylmethoxyimino-5,6,7,8-tetrahydroquinazoline. Example 13 provides a detailed description of how this reaction is conducted.

It should be noted that when the bridging group n is —OCH$_2$—, =NO—, or =NOCH$_2$—, as above, the left end of these moieties is attached to the 6-position of the 2,4-diamino-5,6,7,8-tetrahydroquinazoline ring.

When the bridging group n is —Si(CH$_3$)$_2$—, the Grignard reagent of 8-bromo-1,4-dioxaspiro[4.5]decane is reacted with, for example, chlorodimethylphenylsilane, affording 8-phenyldimethylsilyl-1,4-dioxaspiro[4.5]decane. The 1,4-dioxaspiro functional group is then cleaved from the so-prepared molecule with acetic acid and water, yielding the corresponding 4-(phenyldimethylsilyl)cyclohexanone. The cyclohexanone is then reacted with cyanoguanidine, affording the target 2,4-diamino-6-phenyldimethylsilyl-5,6,7,8-tetrahydroquinazoline. Example 14 provides a detailed description of how this reaction is conducted.

A number of 2-substituted-4-amino-6-substituted-5,6,7,8-tetrahydroquinazolines are prepared (where R is other than amino). A 4-substituted-cyclohexanone, for example 4-(2-chlorophenyl)cyclohexanone, is reacted with N-cyano-S-methylisothiourea (prepared by the method of R. W. Turner; Synthesis, 332 (1975)) under pressure in the presence of pyrrolidine, yielding the targeted 4-amino-2-methylthio-6-substituted-5,6,7,8-tetrahydroquinazoline. The so-prepared 4-amino-2-methylthio-6-substituted-5,6,7,8-tetrahydroquinazoline may in turn be oxidized with 3-chloroperoxybenzoic acid in chloroform, yielding another targeted compound, 4-amino-2-methylsulfinyl-6-substituted-5,6,7,8-tetrahydroquinazoline. Examples 16 and 17 provide detailed descriptions of how these reactions are conducted.

The 4-amino-2-methylsulfinyl-6-substituted-5,6,7,8-tetrahydroquinazoline compounds, for example, 4-amino-2-methylsulfinyl-6-(2-chlorophenyl)-5,6,7,8-tetrahydroquinazoline, may be reacted further with, for example, 40% methylamine or pyrrolidine, under high pressure, yielding the corresponding targeted 4-amino-2-methylamino-6-substituted-5,6,7,8-tetrahydroquinazoline and 4-amino-2-(pyrrolidin-1-yl)-6-substituted-5,6,7,8-tetrahydroquinazoline, respectively. Examples 18 and 19 provide detailed descriptions of how these reactions are conducted.

When a 3,4-disubstituted cyclohexanone is reacted with cyanoguanidine, as described above, the tetrahydroquinazoline product obtained is an isomeric mixture. For example, the reaction of 3-methyl-4-phenylcyclohexanone with cyanoguanidine yields two mixtures of isomers: cis/trans-2,4-diamino-5-methyl-6-phenyl-5,6,7,8-tetrahydroquinazoline and cis/trans-2,4-diamino-7-methyl-6-phenyl-5,6,7,8-tetrahydroquinazoline. Within each family of isomers there also exists a pair of geometric isomers, for example, cis-2,4-diamino-5-methyl-6-phenyl-5,6,7,8-tetrahydroquinazoline and trans-2,4-diamino-5-methyl-6-phenyl-5,6,7,8-tetrahydroquinazoline. Also, within each member of the of the geometric pair, for example, cis-2,4-diamino-5-methyl-6-phenyl-5,6,7,8-tetrahydroquinazoline, there exist additional optical isomers. The scope of the present invention, therefore, is intended to include each geometric and optical isomer as well as the mixtures of these isomers.

The intermediate 3-methyl-4-phenylcyclohexanone is prepared, first by the reaction of 4-phenylcyclohexanone with phenylselenenyl chloride and aqueous 30% hydrogen peroxide, yielding 4-phenyl-2-cyclohexenone, and then the reaction of the cyclohexenone with 1.4M methyllithium and aqueous ammonium chloride, affording 3-methyl-4-phenylcyclohexanone. The cyclohexanone is then reacted with cyanoguanidine as previously described. Example 15 provides a detailed description of how this reaction is conducted.

EXAMPLES

The following examples are by way of illustration only, and are not intended to limit the scope of the invention claimed herein.

The products of these examples are summarized in Table 1 below.

EXAMPLE 1

SYNTHESIS OF 2,4-DIAMINO-6-(1,1-DIMETHYLETHYL)-5,6,7,8-TETRAHYDROQUINAZOLINE (COMPOUND 4)

A reaction vessel equipped with a Dean Stark trap was charged with 11.8 grams (0.075 mole) of 4-(1,1-dimethylethyl)cyclohexanone and 4.2 grams (0.050 mole) of cyanoguanidine in 20 mL of 2-(2-ethoxyethoxy)ethanol. The mixture was heated incrementally at 80° C., 100° C., 140° C. and 160° C., the latter where it was stirred for about 18 hours. The reaction mixture was then cooled to ambient temperature, where it solidified. The reaction mixture was triturated with 30 mL of diethyl ether, and the resultant solid was collected by filtration. The solid was washed several times with diethyl ether, yielding, when dried, 4.5 grams of 2,4-diamino-6-(1,1-dimethylethyl)-5,6,7,8-tetrahydroquinazoline, mp>250° C. The NMR spectrum was consistent with the proposed structure.

EXAMPLE 2

SYNTHESIS OF 2,4-DIAMINO-6-(2-CHLOROPHENYLMETHYL)-5,6,7,8-TETRAHYDROQUINAZOLINE (COMPOUND 53)

Step A Synthesis of 2- chlorophenylmethyltriphenylphosphonium bromide as an intermediate Under a nitrogen atmosphere, a solution of 10.0 grams (0.049 mole) of 2-chlorophenylmethyl bromide and 13.0 grams (0.050 mole) of triphenylphosphine in about 100 mL of toluene was heated at reflux for about 18 hours. The reaction mixture was cooled, and a solid was collected by filtration. The solid was washed with toluene and dried under vacuum, yielding 22.8 grams of 2-chlorophenylmethyltriphenylphosphonium bromide, mp>250° C.

Step B Synthesis of 8-(2-chlorophenylmethylene)-1,4-dioxaspiro[4.5]decane as an intermediate A stirred solution of 18.0 grams (0.039 mole) of 2-chlorophenylmethyltriphenylphosphonium bromide in about 50 mL of dry tetrahydrofuran was cooled in a dry ice-acetone bath, and 15.4 mL (0.039 mole) of n-butyllithium (2.5M in hexanes) was added dropwise. Upon completion of addition, the reaction mixture was stirred for 1 hour. After this time a solution of 5.0 grams (0.032 mole) of 1,4-cyclohexanedione mono-ethylene ketal in about 5.0 mL of dry tetrahydrofuran was added dropwise. Upon completion of addition, the reaction mixture was allowed to warm to ambient temperature where it was stirred for about 18 hours. After this time the reaction mixture was concentrated under reduced pressure, yielding about 6.9 grams of 8-(2-chlorophenylmethylene)-1,4-dioxaspiro[4.5]-decane. The NMR spectrum was consistent with the proposed structure.

Step C Synthesis of 8-(2-chlorophenylmethyl)-1,4-dioxaspiro[4.5]decane as an intermediate A solution of 6.9 grams (0.026 mole) of 8-(2-chlorophenylmethylene)-1,4-dioxaspiro[4.5]decane in about 50 mL of ethanol and 0.4 gram (catalyst) of 10% palladium on charcoal were placed in a hydrogenation bottle and hydrogenated using a Parr hydrogenation apparatus. Upon the theoretical uptake of hydrogen, the reaction mixture was filtered to remove the catalyst. The filtrate was concentrated under reduced pressure to a residue. The residue was subjected to column chromatography using silica gel. Elution was accomplished using 33% ethyl acetate in hexane. The product-containing fractions were combined and concentrated under reduced pressure, yielding 5.0 grams of 8-(2-chlorophenylmethyl)-1,4-dioxaspiro[4.5]decane. The NMR spectrum was consistent with the proposed structure.

Step D Synthesis of 4-(2-chlorophenylmethyl) cyclohexanone as an intermediate

A mixture of 4.8 grams (0.018 mole) of 8-(2-chlorophenylmethyl)-1,4-dioxaspiro[4.5]decane in 25 mL of water and 100 mL of acetic acid was stirred at ambient temperature for about 18 hours. After this time the reaction mixture was carefully partitioned between diethyl ether and an aqueous solution saturated with sodium bicarbonate. The combined ether extracts were then washed with an aqueous solution saturated with sodium chloride. The organic layer was then added with magnesium sulfate and filtered. The filtrate was concentrated under reduced pressure, yielding 3.1 grams of 4-(2-chlorophenylmethyl)cyclohexanone, mp 48° C. The NMR spectrum was consistent with the proposed structure.

Step E Synthesis of 2,4-diamino-6-(2-chlorophenylmethyl)-5,6,7,8-tetrahydroquinazoline (Compound 53)

This compound was prepared in a manner analogous to that of Example 1, using 2.9 grams (0.013 mole) of 4-(2-chlorophenylmethyl)cyclohexanone and 1.2 grams (0.014 mole) of cyanoguanidine in 2-(2-ethoxyethoxy)ethanol. The yield of 2,4-diamino-6-(2-chlorophenylmethyl)-5,6,7,8-tetrahydroquinazoline was 0.3 gram, mp 134° C. The NMR spectrum was consistent with the proposed structure.

EXAMPLE 3

SYNTHESIS OF 2,4-DIAMINO-6-(3,5-DICHLOROPHENYLMETHYL)-5,6,7,8-TETRAHYDROQUINAZOLINE
(COMPOUND 59)

Step A Synthesis of 3,5-dichlorophenylmethyl chloride as an intermediate

Under a nitrogen atmosphere, a stirred solution of 25.0 grams (0.141 mole) of 3,5-dichlorophenylmethyl and 11.4 mL (0.141 mole) of pyridine in 200 mL of chloroform was cooled to 5° C., and 15.9 mL (0.218 mole) of thionyl chloride was added dropwise during a 10 minute period. Upon completion of addition, the reaction mixture was allowed to warm to ambient temperature where it was stirred for about 18 hours. After this time, the reaction mixture was poured into 300 mL of water, and the mixture was extracted with 600 mL of diethyl ether. The ether solution was washed with 70 mL of an aqueous 6N hydrochloric acid solution, and then it was concentrated under reduced pressure to a residual oil. The oil was distilled under reduced pressure, yielding 25.6 grams of 3,5-dichlorophenylmethyl chloride, bp 95°–100° C./0.1 mm Hg.

Step B Synthesis of 3,5-dichlorophenylmethyltriphenylphosphonium chloride as an intermediate This compound was prepared in a manner analogous to that of Step A of Example 2, using 25.6 grams (0.131 mole) of 3,5-dichlorophenylmethyl chloride and 34.1 grams (0.130 mole) of triphenylphosphine in 250 mL of toluene. The yield of 3,5-dichlorophenylmethyltriphenylphosphonium chloride was 46.0 grams.

Step C Synthesis of 8-(3,5-dichlorophenylmethylene)-1,4-dioxaspiro[4.5]decane as an intermediate Under a nitrogen atmosphere, a stirred mixture of 4.2 grams (0.11 mole) of sodium hydride (60% in mineral oil) in 200 mL of anhydrous dimethyl sulfoxide was heated to about 90° C. where it was maintained for 10 minutes. After this time the reaction mixture was cooled to 25° C., and 46.0 grams (0.10 mole) of 3,5-dichlorophenylmethyltriphenylphosphonium chloride was added, followed by 14.0 grams (0.10 mole) of 1,4-cyclohexanedione mono-ethylene ketal. Upon completion of addition the reaction mixture was again warmed to 90° C., then it was allowed to cool to ambient temperature. After this time the reaction mixture was poured into 400 mL of water, and the mixture was extracted with two 250 mL portions of diethyl ether. The combined extracts were then washed with two 100 mL portions of water. The organic layer was concentrated under reduced pressure to an oily solid residue. The oily solid was taken up in a solution of 90 mL of petroleum ether and 10 mL of diethyl ether, and filtered. The filtrate was concentrated under reduced pressure to a residue. The residue was subjected to column chromatography using silica gel. Elution was accomplished using 10% diethyl ether in petroleum ether. The product-containing fractions were combined and concentrated under reduced pressure, yielding 9.7 grams of 8-(3,5-dichlorophenylmethylene)-1,4-dioxaspiro[4.5]decane, mp about 66° C. The NMR spectrum was consistent with the proposed structure.

Step D Synthesis of 4-(3,5-dichlorophenylmethylene) cyclohexanone as an intermediate This compound was prepared in a manner analogous to that of Step D of Example 2, using 9.1 grams (0.030 mole) of 8-(3,5-dichlorophenylmethylene)-1,4-dioxaspiro[4.5] decane and 25 mL of water in 50 mL of acetic acid. The yield of 4-(3,5-dichlorophenylmethylene)cyclohexanone was 7.6 grams. The NMR spectrum was consistent with the proposed structure.

Step E Synthesis of 4-(3,5-dichlorophenylmethyl) cyclohexanol as an intermediate A mixture of 7.5 grams (0.031 mole) of 4-(3,5-dichlorophenylmethylene)cyclohexanone and 1.0 gram (catalyst) of 10% palladium on charcoal (Degussa type) in 100 mL of ethanol was placed in a hydrogenation bottle and hydrogenated using a Parr hydrogenation apparatus. Upon completion of 2 hours at 50 psi, the reaction had used 25% of the theoretical amount of hydrogen. After this time the reaction mixture was filtered, and an aliquot was concentrated under reduced pressure to a residue. An NMR spectrum indicated that complete hydrogenation had not taken place. The hydrogenation was again conducted using the cyclohexanone above, and 1.0 gram of fresh 10% palladium on charcoal in 100 mL of ethanol. Upon the uptake of the theoretical amount of hydrogen, the reaction mixture was filtered. The filtrate was allowed to stand about 60 hours and then was concentrated under reduced pressure, yielding 7.3 grams of 4-(3,5-dichlorophenylmethyl)cyclohexanol. The NMR spectrum was consistent with the proposed structure.

Step F Synthesis of 4-(3,5-dichlorophenylmethyl) cyclohexanone as an intermediate A solution of chromic acid was prepared using 5.6 grams of sodium dichromate, 16.8 mL of water, 4.1 mL of concentrated sulfuric acid, and additional water to provide 28 mL of solution. The sodium chromate solution was cooled to 0° C. and was added dropwise to a stirred, cold (0° C.) solution of 7.3 grams (0.028 mole) of 4-(3,5-dichlorophenylmethyl)cyclohexanol in 15 mL of diethyl ether. The complete addition required about 5 minutes. Upon completion of addition, the reaction mixture was stirred for 5 minutes and then was extracted with diethyl ether. The ether extract was washed with an aqueous solution saturated with sodium bicarbonate, then with water. The organic layer was concentrated under reduced pressure, yielding 2.6 grams of 4-(3,5-dichlorophenylmethyl)cyclohexanone.

Step G Synthesis of 2,4-diamino-6-(3,5-dichlorophenylmethyl)-5,6,7,8-tetrahydroquinazoline (Compound 59)

This compound was prepared in a manner analogous to that of Example 1, using 2.6 grams (0.01 mole) of 4-(3,5-dichlorophenylmethyl)cyclohexanone and 0.8 gram (0.01 mole) of cyanoguanidine. A small sample of the crude product was recrystallized from a mixture of dimethyl sulfoxide and methanol, giving a solid, mp>200° C. The yield of 2,4-diamino-6-(3,5-dichlorophenylmethyl)-5,6,7,8-tetrahydroquinazoline was 2.3 grams. The NMR spectrum was consistent with the proposed structure.

EXAMPLE 4

SYNTHESIS OF 2,4-DIAMINO-6-PHENYL-5,6,7,8-TETRAHYDROQUINAZOLINE (COMPOUND 9)

This compound was prepared in a manner analogous to that of Example 1, using 4.2 grams (0.05 mole) of cyanoguanidine and 13.1 grams (0.08 mole) of 4-phenylcyclohexanone. The crude product was recrystallized from ethanol, yielding 2,4-diamino-6-phenyl-5,6,7,8-tetrahydroquinazoline, mp 223°–226° C. The NMR spectrum was consistent with the proposed structure.

EXAMPLE 5

SYNTHESIS OF 2,4-DIAMINO-6-(2,3-DIHYDRO-2,2-DIMETHYLBENZOFURAN-7-YLMETHYL)-5,6,7,8-TETRAHYDROQUINAZOLINE (COMPOUND 77)

Step A Synthesis of 2,3-dihydro-2,2-dimethylbenzofuran-7-ylmethyl bromide as an intermediate Under a nitrogen atmosphere, a mixture of 8.7 grams (0.1 mole) of lithium bromide in 100 mL of acetonitrile is stirred, and 13.5 grams (0.125 mole) of trimethylsilyl chloride is added. Upon completion of addition, a solution of 8.9 grams (0.05 mole) of 2,3-dihydro-2,2-dimethylbenzofuran-7-ylmethanol in 50 mL of acetonitrile is added. Upon completion of addition, the reaction mixture is warmed to reflux, where it is stirred for about 18 hours. After this time the reaction mixture is cooled to ambient temperature and then is taken up in 200 mL of diethyl ether. The mixture is then washed with 25 mL of water and then with 25 mL of an aqueous solution saturated with sodium chloride. The organic layer is then dried with magnesium sulfate and filtered. The filtrate is concentrated under reduced pressure to a residue, yielding 2,3-dihydro-2,2-dimethylbenzofuran-7-ylmethyl bromide.

Step B Synthesis of (2,3-dihydro-2,2-dimethylbenzofuran-7-ylmethyl)triphenylphosphonium bromide as an intermediate This compound is prepared in a manner analogous to that of Step A of Example 2, using 11.8 grams (0.049 mole) of 2,3-dihydro-2,2-dimethylbenzofuran-7-ylmethyl bromide and 13.0 grams (0.050 mole) of triphenylphosphine in about 100 mL of toluene, yielding (2,3-dihydro-2,2-dimethylbenzofuran-7-ylmethyl)triphenylphosphonium bromide.

Step C Synthesis of 8-(2,3-dihydro-2,2-dimethylbenzofuran-7-ylmethylene)-1,4-dioxaspiro[4.5]decane as an intermediate This compound is prepared in a manner analogous to that of Step B of Example 2, using 18.4 grams (0.039 mole) of (2,3-dihydro-2,2-dimethylbenzofuran-7-ylmethyl)triphenylphosphonium bromide, 15.4 mL (0.039 mole) of n-butyllithium (2.5M in hexanes), and 5.0 grams (0.032 mole) of 1,4-cyclohexanedione mono-ethylene ketal in about 55 mL of dry tetrahydrofuran, yielding 8-(2,3-dihydro-2,2-dimethylbenzofuran-7-ylmethylene)-1,4-dioxaspiro[4.5]decane Step D Synthesis of 8-(2,3-dihydro-2,2-dimethylbenzofuran-7-ylmethyl)-1,4-dioxaspiro[4.5]decane as an intermediate This compound is prepared in a manner analogous to that of Step C of Example 2, by the hydrogenation of 7.8 grams (0.026 mole) of 8-(2,3-dihydro-2,2-dimethylbenzofuran-7-ylmethylene)-1,4-dioxaspiro[4.5]decane in the presence of 0.4 gram (catalyst) of 10% palladium on charcoal in 50 mL of ethanol, yielding 8-(2,3-dihydro-2,2-dimethylbenzofuran-7-ylmethyl)-1,4-dioxaspiro[4.5]decane.

Step E Synthesis of 4-(2,3-dihydro-2,2-dimethylbenzofuran-7-ylmethyl)cyclohexanone as an intermediate This compound is prepared in a manner analogous to that of Step D of Example 2, using 5.4 grams (0.01 8 mole) of 8-(2,3-dihydro-2,2-dimethylbenzofuran-7-ylmethyl)-1,4-dioxaspiro[4.5]decane and 25 mL of water in 100 mL of acetic acid, yielding 4-(2,3-dihydro-2,2-dimethylbenzofuran-7-ylmethyl)cyclohexanone.

Step F Synthesis of 2,4-diamino-6-(2,3-dihydro-2,2-dimethylbenzofuran-7-ylmethyl)-5,6,7,8-tetrahydroquinazoline (Compound 77)

This compound is prepared in a manner analogous to that of Example 1, using 3.4 grams (0.013 mole) of 4-(2,3-dihydro-2,2benzofuran-7-ylmethyl)cyclohexanone and 1.2 grams (0.014 mole) of cyanoguanidine in 2-(2-ethoxyethoxy)ethanol, yielding 2,4-diamino-6-(2,3-dihydro-2,2-dimethylbenzofuran-7-ylmethyl)-5,6,7,8-tetrahydroquinazoline.

EXAMPLE 6

SYNTHESIS OF 2,4-DIAMINO-6-(2,2,3,3-TETRAFLUORO-2,3-DIHYDROBENZOFURAN-7-YLMETHYL)-5,6,7,8-TETRAHYDROQUINAZOLINE (COMPOUND 80)

Step A Synthesis of 2,2,3,3-tetrafluoro-2,3-dihydrobenzofuran-7-ylmagnesium chloride as an intermediate Under a dry nitrogen atmosphere, a stirred mixture of 13.1 grams (0.54 mole) of magnesium turnings in 75 mL of dry tetrahydrofuran is maintained at gentle reflux, and a solution of 113.3 grams (0.50 mole) of 2,2,3,3-tetrafluoro-2,3-dihydrobenzofuran-7-yl chloride (prepared as disclosed in Example 6 of U.S. Pat. No. 4,772,730) in 75 mL of dry tetrahydrofuran is added dropwise during a two hour period. Upon completion of addition, the reaction mixture is heated at reflux for an additional five hours and then is allowed to cool to ambient temperature as it stood for about 18 hours.

Step B Synthesis of 2,2,3,3-tetrafluoro-2,3-dihydrobenzofuran-7-ylmethanol as an intermediate Under a nitrogen atmosphere, the reaction mixture from above is decanted into a clean, dry reaction vessel, leaving the unreacted magnesium turnings in the first vessel. This solution containing 2,2,3,3-tetrafluoro-2,3-dihydrobenzofuran-7-ylmagnesium chloride is heated at reflux, and 16.5 grams (0.55 mole based on formaldehyde) of polyoxymethylene diacetate (avg. mol. wgt. approx. 50,000, commercially available from E. I. du Pont De Nemours & Co., Inc. Wilmington Del., under the trade name Delrin 500 acetal homopolymer resin), milled to about 80 mesh, is added with stirring during about a three hour period. Upon completion of addition, the reaction mixture is heated at reflux for an additional four hours and then is allowed to cool to ambient temperature as it stood for about 18 hours. The reaction mixture is warmed to about 53° C. and then is poured into 100 grams of ice, 52 grams of concentrated hydrochloric acid, and 200 grams of a mixture of 95% n-octane and 5% toluene (wt/wt). This mixture is filtered, and the organic layer is separated. The organic layer is concentrated under reduced pressure, yielding 2,2,3,3-tetrafluoro-2,3-dihydrobenzofuran-7-ylmethanol.

NOTE:

The procedure to prepare 2,2,3,3-tetrafluoro-2,3-dihydrobenzofuran-7-ylmethanol is disclosed in U.S. Pat. No. 4,470,637).

Step C Synthesis of 2,2,3,3-tetrafluoro-2,3-dihydrobenzofuran-7-ylmethyl bromide as an intermediate This compound is prepared in a manner analogous to that of Step A of Example 5, using 11.1 grams (0.05 mole) of 2,2,3,3-tetrafluoro-2,3-dihydrobenzofuran-7-ylmethanol, 8.7 grams (0.1 mole) of lithium bromide, and 13.5 grams (0.125 mole) of trimethylsilyl chloride in 100 mL of acetonitrile, yielding 2,2,3,3-tetrafluoro-2,3-dihydrobenzofuran-7-ylmethyl bromide.

Step D Synthesis of (2,2,3,3-tetrafluoro-2,3-dihydrobenzofuran-7-ylmethyl)triphenylphosphonium bromide as an intermediate This compound is prepared in a manner analogous to that of Step A of Example 2, using 14.0 grams (0.049 mole) of 2,2,3,3-tetrafluoro-2,3-dihydrobenzofuran-7-ylmethyl bromide and 13.0 grams (0.050 mole) of triphenylphosphine in about 100 mL of toluene, yielding (2,2,3,3-tetrafluoro-2,3-dihydrobenzofuran-7-ylmethyl)triphenylphosphonium bromide.

Step E Synthesis of 8-(2,2,3,3-tetrafluoro-2,3-dihydrobenzofuran-7-ylmethylene)-1,4-dioxaspiro[4.5]decane as an intermediate This compound is prepared in a manner analogous to that of Step B of Example 2, using 20.1 grams (0.039 mole) of (2,2,3,3-tetrafluoro-2,3-dihydrobenzofuran-7ylmethyl)triphenylphosphonium bromide, 15.4 mL (0.0) 39 mole) of n-butyllithium (2.5M in hexanes), and 5.0 grams (0.032 mole) of 1,4-cyclohexanedione mono-ethylene ketal in about 55 mL of dry tetrahydrofuran, yielding 8-(2,2,3,3-tetrafluoro-2,3-dihydrobenzofuran-7-ylmethylene)-1,4-dioxaspiro[4.5]decane.

Step F Synthesis of 8-(2,2,3,3-tetrafluoro-2,3-dihydrobenzofuran-7-ylmethyl)-1,4-dioxaspiro[4.5]decane as an intermediate This compound is prepared in a manner analogous to that of Step C of Example 2, by the hydrogenation of 8.9 grams (0.026 mole) of 8-(2,2,3,3-tetrafluoro-2,3-dihydrobenzofuran-7-ylmethylene)-1,4-dioxaspiro[4.5]decane in the presence of 0.4 gram (catalyst) of 10% palladium on charcoal in 50 mL of ethanol, yielding 8-(2,2,3,3-tetrafluoro-2,3-dihydrobenzofuran-7-ylmethyl)-1,4-dioxaspiro[4.5]decane.

Step G Synthesis of 4-(2,2,3,3-tetrafluoro-2,3-dihydrobenzofuran-7-ylmethyl)cyclohexanone as an intermediate This compound is prepared in a manner analogous to that of Step D of Example 2, using 6.2 grams (0.018 mole) of 8-(2,2,3,3-tetrafluoro-2,3-dihydrobenzofuran-7-ylmethyl)-1,4-dioxaspiro[4.5]decane and 25 mL of water in 100 mL of acetic acid, yielding 4-(2,2,3,3-tetrafluoro-2,3-dihydrobenzofuran-7-ylmethyl)cyclohexanone.

Step H Synthesis of 2,4-diamino-6-(2,2,3,3-tetrafluoro-2,3-dihydrobenzofuran-7-ylmethyl)-5,6,7,8-tetrahydroquinazoline (compound 80)

This compound is prepared in a manner analogous to that of Example 1, using 3.9 grams (0.013 mole) of 4-(2,2,3,3-tetrafluoro-2,3-dihydrobenzofuran-7-ylmethyl)cyclohexanone and 1.2 grams (0.014 mole) of cyanoguanidine in 2-(2-ethoxyethoxy)ethanol, yielding 2,4-diamino-6-(2,2,3,3-tetrafluoro-2,3-dihydrobenzofuran-7-ylmethyl)-5,6,7,8-tetrahydroquinazoline.

EXAMPLE 7

SYNTHESIS OF 2,4-DIAMINO-6-[2-(3-CHLOROPHENYL)PROPAN-2-YL]-5,6,7,8-TETRAHYDROQUINAZOLINE (COMPOUND 97)

Step A Synthesis of methyl 3-chlorophenyl ketone as an intermediate

Under a nitrogen atmosphere, 36.7 mL (0.11 mole) of methylmagnesium bromide (3.0M in diethyl ether) is stirred, and a solution of 13.8 grams (0.10 mole) of 3-chlorobenzonitrile in 50 mL of dry tetrahydrofuran is added slowly dropwise. Upon completion of addition, the reaction mixture is warmed to reflux where it is stirred for about 18 hours. After this time the reaction mixture is cooled to ambient temperature, and about 40 mL of methanol is added dropwise. Upon completion of addition, the reaction mixture is stirred for two hours and then filtered. The filtrate is then stirred for about 18 hours with 35 grams of silica gel and 100 mL of water. The mixture is filtered, and the filtrate is diluted with ethyl acetate. The mixture is then washed with water, and the organic layer is dried with magnesium sulfate. The mixture is filtered, and the filtrate is concentrated under reduced pressure, yielding methyl 3-chlorophenyl ketone.

Step B Synthesis of 2-(3-chlorophenyl)propan-2-ol as an intermediate

This compound is prepared in a manner analogous to that of Step A of this Example, using 13.9 grams (0.09 mole) of methyl 3-chlorophenyl ketone and 33.3 mL of methylmagnesium bromide (3.0M in diethyl ether) in 50 mL of dry tetrahydrofuran, yielding 2-(3-chlorophenyl)propan-2-ol.

Step C Synthesis of 2-bromo-2-(3-chlorophenyl)propane as an intermediate

This compound is prepared in a manner analogous to that of Step A of Example 5, using 8.5 grams (0.05 mole) of 2-(3-chlorophenyl)propan-2-ol, 8.7 grams (0.1 mole) of lithium bromide, and 13.5 grams (0.125 mole) of trimethylsilyl chloride in 100 mL of acetonitrile, yielding 2-bromo-2-(3-chlorophenyl)propane.

Step D Synthesis of 1-[2-(3-chlorophenyl)propan-2-yl]-1-cyclohexen-4-one as an intermediate The Grignard reagent of 2-bromo-2-(3-chlorophenyl)propane is prepared by adding dropwise a solution of 9.3 grams (0.040 mole) of 2-bromo-2-(3-chlorophenyl)propane in 45 mL of dry tetrahydrofuran to 1.1 grams (0.044 mole) of magnesium turnings in 25 mL of refluxing tetrahydrofuran. Upon completion of addition, the Grignard reagent is stirred at reflux for one hour. The reaction mixture is then cooled in an ice-water bath, and a solution of 6.2 grams (0.040 mole) of 1,4-cyclohexanedione mono-ethylene ketal in about 25 mL of tetrahydrofuran is added dropwise. Upon completion of addition, the reaction mixture is allowed to warm to ambient temperature where it is stirred for about 18 hours. After this time the reaction is quenched by the addition of 100 mL of aqueous 10% hydrochloric acid. The reaction mixture is stirred for 10 minutes and then is extracted with two 50 mL portions of diethyl ether. The combined extracts are washed with 10 mL of water and then are dried with magnesium sulfate. The mixture is filtered and concentrated under reduced pressure, yielding 1-[2-(3-chlorophenyl)propan-2-yl]-1-cyclohexen-4-one.

Step E Synthesis of 4-[2-(3-chlorophenyl)propan-2-yl] cyclohexanone as an intermediate This compound is prepared in a manner analogous to that of Step C of Example 2, by the hydrogenation of 6.5 grams (0.026 mole) of 1-[2-(3-chlorophenyl)propan-2-yl]-1-cyclohexen-4-one in the presence of 0.4 gram (catalyst) of 10% palladium on charcoal in 50 mL of ethanol, yielding 4-[2-(3-chlorophenyl)propan-2-yl]cyclohexanone.

Step F Synthesis of 2,4-diamino-6-[2-(3-chlorophenyl) propan-2-yl]-5,6,7,8-tetrahydroquinazoline (compound 97)

This compound is prepared in a manner analogous to that of Example 1, using 3.2 grams (0.013 mole) of 4-[2-(3-chlorophenyl)propan-2-yl]cyclohexanone and 1.2 grams (0.014 mole) of cyanoguanidine in 2-(2-ethoxyethoxy) ethanol, yielding 2,4-diamino-6-[2-(3-chlorophenyl)propan-2-yl]-5,6,7,8-tetrahydroquinazoline.

EXAMPLE 8

SYNTHESIS OF 2,4-DIAMINO-6-[1-CHLORO-2-[3,5-DI(TRIFLUOROMETHYL)PHENYL] ETHENYL]-5,6,7,8-TETRAHYDROQUINAZOLINE (COMPOUND 142)

Step A Synthesis of 3,5-di(trifluoromethyl)phenyl iodide as an intermediate

Under a nitrogen atmosphere, a stirred solution of 15.0 grams (0.051 mole) of 3,5-di(trifluoromethyl)phenyl bromide in 45 mL of dry tetrahydrofuran was cooled to below −80° C., and 20.5 mL (0.051 mole) of n-butyllithium (2.5M in hexanes) was added dropwise while maintaining the reaction mixture temperature below −80° C. Upon completion of addition, an additional 50 mL of tetrahydrofuran was added to promote stirring. The reaction mixture was then stirred at −80° C. for an additional one hour. After this time a solution of 13.0 grams (0.051 mole) of iodine in 30 mL of tetrahydrofuran was added dropwise while maintaining the reaction mixture temperature below −80° C. Upon completion of addition, the reaction mixture was allowed to warm to ambient temperature. The reaction mixture was then poured into 400 mL of water, and the mixture was extracted with one 200 mL portion of diethyl ether. The ether extract was washed with an aqueous solution of 10% meta-sodium bisulfate. The organic layer was dried with magnesium sulfate and filtered. The filtrate was concentrated under reduced pressure, yielding 13.1 grams of 3,5-di (trifluoromethyl)phenyl iodide.

Step B Synthesis of 1,4-dioxaspiro[4.5]decan-8-ol as an intermediate

A solution of 15.6 grams (0.10 mole) of 1,4-cyclohexanedione mono-ethylene ketal in about 40 mL of ethanol is stirred, and 1.9 grams (0.05 mole) of sodium borohydride is added portionwise during a one hour period. Upon completion of addition, the reaction mixture is stirred at ambient temperature for about four hours. After this time the reaction mixture is concentrated under reduced pressure to a residue. The residue is taken up in about 40 mL of water, and the mixture is extracted with three 25 mL portions of diethyl ether. The combined extracts are washed with an aqueous solution saturated with sodium chloride. The organic layer is then dried with magnesium sulfate and filtered. The filtrate is concentrated under reduced pressure, yielding 1,4-dioxaspiro-[4.5]decan-8-ol Step C Synthesis of 8-methylsulfonyloxy-1,4-dioxaspiro [4.5]decane as an intermediate A stirred solution of 14.2 grams (0.090 mole) of 1,4-dioxaspiro[4.5]decan-8-ol and 10.0 grams (0.099 mole) of triethylamine in 100 mL of methylene chloride is cooled to 0° C., and a solution of 7.7 mL (0.099 mole) of methanesulfonyl chloride in 25 mL of methylene chloride is added drop-wise at a rate to maintain the reaction mixture temperature at 0° C. to 5° C. Upon completion of addition, the reaction mixture is allowed to warm to ambient temperature. The reaction mixture is then washed with two 75 mL portions of an aqueous 5% sodium bicarbonate solution and then with 75 mL of an aqueous solution saturated with sodium chloride. The organic layer is dried with magnesium sulfate and filtered. The filtrate is concentrated under reduced pressure, yielding 8-methylsulfonyloxy-1,4-dioxaspiro[4.5]decane Step D Synthesis of 8-trimethylsilylethyl-1,4-dioxaspiro [4.5]decane as an intermediate Under a nitrogen atmosphere, a mixture of 3.2 grams (0.08 mole) of sodium hydride (60% in mineral oil) in 25 mL of tetrahydrofuran is stirred, and a solution of 7.9 grams (0.08 mole) of trimethylsilylacetylene in 15 mL of tetrahydrofuran is added dropwise. Upon completion of addition, the reaction mixture is stirred at ambient temperature for about one hour. The reaction mixture is then cooled to 0° C., and a solution of 18.9 grams (0.08 mole) of 8-methylsulfonyloxy-1,4-dioxaspiro[4.5]decane in 25 mL of tetrahydrofuran is added dropwise. Upon completion of addition, the reaction mixture is allowed to warm to ambient temperature where it is stirred during about 18 hours. After this time the reaction mixture is concentrated under reduced pressure to a residue. The residue is stirred in water, and the mixture is extracted with three 50 mL portions of diethyl ether. The combined extracts are washed with water and dried with magnesium sulfate. The mixture is filtered, and the filtrate is concentrated under reduced pressure, yielding 8-trimethylsilylethynyl-1,4-dioxaspiro[4.5]decane.

Step E Synthesis of 8-ethynyl-1,4-dioxaspiro[4.5]decane as an intermediate

A mixture of 16.7 grams (0.07 mole) of 8-trimethylsilylethynyl-1,4-dioxaspiro[4.5]decane and 1.1 grams (0.07 mole) of potassium carbonate in 200 mL of methanol is stirred at ambient temperature for about one hour. The reaction mixture is then concentrated under reduced pressure to a residue. The residue is stirred in about 150 mL of water, and the mixture is extracted with three 150 mL portions of diethyl ether. The combined extracts are dried with magnesium sulfate and filtered. The filtrate is concentrated under reduced pressure, yielding 8-ethynyl-1,4-dioxaspiro[4.5]decane.

Step F Synthesis of 4-[3,5-di(trifluoromethyl) phenylethynyl]cyclohexanone as an intermediate A solution of 3.9 grams (0.022 mole) of 8-ethynyl-1,4-dioxaspiro[4.5]decane, 10.5 grams (0.031 mole) of 3,5-di(trifluoromethyl)phenyl iodide (prepared in Step A of this Example), 10.7 grams (0.077 mole) of triethylamine, 0.5 gram (catalyst) of bis(triphenylphosphine)palladium(II) chloride, and 0.5 gram (catalyst) of copper(I) iodide in 100 mL of acetonitrile is stirred at ambient temperature for about 18 hours. After this time the reaction mixture is concentrated under reduced pressure to a residue. The residue is then stirred for about 2 hours with 150 mL of aqueous 1N hydrochloric acid. After this time the mixture is extracted with three 100 mL portions of ethyl acetate. The combined extracts are washed with an aqueous solution of 10% lithium chloride. The organic layer is dried with magnesium sulfate and filtered. The filtrate is concentrated under reduced pressure, yielding 4-[3,5-di(trifluoromethyl)phenylethynyl] cyclohexanone.

Step G Synthesis of 2,4-diamino-6-[3,5-di(trifluoromethyl) phenylethynyl]-5,6,7,8-tetrahydroquinazoline as an intermediate This compound is prepared in a manner analogous to that of Example 1, using 4.3 grams (0.013 mole) of 4-[3,5-di(trifluoromethyl)phenylethynyl]cyclohexanone and 1.2 grams (0.01 4 mole) of cyanoguanidine in 2-(2-ethoxyethoxy)ethanol, yielding 2,4-diamino-6-[3,5-di(trifluoromethyl phenylethynyl]-5,6,7,8-tetrahydroquinazoline.

Step H Synthesis of 2,4-diamino-6-[1-chloro-2-[3,5-di(trifluoromethyl)phenyl]ethenyl]-5,6,7,8-tetrahydroquinazoline (Compound 142)

A stirred mixture of 3.6 grams (0.009 mole) of 2,4-diamino-6-[3,5-di(trifluoromethyl)phenylethynyl]-5,6,7,8-tetrahydroquinazoline and 1.2 grams (0.009 mole) of triethylammonium hydrogen dichloride (prepared by the method of J. Cousseau et al., JCS Faraday II, 1973, 1821 is heated at about 65° C. for a period of 24 to 27 hours. After this time the reaction mixture is stirred with water and is extracted with three 50 mL portions of diethyl ether. The combined extracts are dried with magnesium sulfate and filtered. The filtrate is concentrated under reduced pressure, yielding 2,4-diamino-6-[1-chloro-2-[3,5-di(trifluoromethyl) phenyl]ethenyl]-5,6,7,8-tetrahydroquinazoline.

NOTE: The procedure to prepare 2,4-diamino-6-[1-chloro-2-[3,5-di(trifluoromethyl)phenyl]ethenyl]-5,6,7,8-tetrahydroquinazoline is disclosed by J. Coueseau et al., JCS Perkin I, 1977, 1797.

EXAMPLE 9

SYNTHESIS OF 2,4-DIAMINO-6-(3-TRIFLUOROMETHYLPHENYL)CARBONYL-5,6,7,8-TETRAHYDROQUINAZOLINE (COMPOUND 174)

Step A Synthesis of 8-bromo-1,4-dioxaspiro[4.5]decane as an intermediate

A stirred solution of 17.4 grams (0.11 mole) of 1,4-dioxaspiro[4.5]decan-8-ol (prepared as in Step B of Example 8) and 46.2 grams (0.14 mole) of freshly recrystallized carbon tetrabromide in 100 mL of methylene chloride is cooled to about 0° C., and a solution of 32.3 grams (0.12 mole) of triphenylphosphine in 50 mL of methylene chloride is added dropwise. Upon completion of addition, the reaction mixture is allowed to warm to ambient temperature where it is stirred for about 18 hours. After this time the reaction mixture is concentrated to about one quarter of the original volume. The concentrate is then passed through a pad of silica gel. Elution is accomplished with heptane. The eluate is concentrated under reduced pressure, yielding 8-bromo-1,4-dioxaspiro[4.5]decane.

NOTE: The procedure to prepare 8-bromo-1,4-dioxaspiro [4.5]decane is disclosed by E. I. Snyder et al.; JOC, 36, 403 (1971)

Step B Synthesis of the Grignard reagent of 8-bromo-1,4-dioxaspiro[4.5]decane as an intermediate This compound is prepared in a manner analogous to that of Step A of Example 6, using 22.1 grams (0.10 mole) of 8-bromo-1,4-dioxaspiro[4.5]decane and 2.7 grams (0.11 mole) of magnesium turnings in 100 mL of tetrahydrofuran, yielding the Grignard reagent of 8-bromo-1,4-dioxaspiro [4.5]decane.

Step C Synthesis of (1,4-dioxaspiro[4.5]decan-8-yl)(3-trifluoromethylphenyl)]methanol as an intermediate This compound is prepared in a manner analogous to that of Step B of Example 6, using 22.1 grams (0.09 mole) of the Grignard reagent of 8-bromo-1,4-dioxaspiro[4.5]decane and 17.4 grams (0.10 mole) of 3-trifluoromethylbenzaldehyde in tetrahydrofuran. Upon completion of the reaction, the reaction mixture is poured into a mixture of 100 grams of ice, 100 mL of an aqueous solution saturated with ammonium chloride, and 200 mL of diethyl ether. This mixture is filtered and the organic layer is separated. The organic layer is concentrated under reduced pressure, yielding [(1,4-dioxaspiro[4.5]decan-8-yl)(3-trifluoromethylphenyl)] methanol.

Step D Synthesis of phenylmethyl [(1,4-dioxaspiro[4.5] decan-8-yl)(3-trifluoromethylphenyl)]methyl ether as an intermediate A suspension of 3.3 grams (0.084 mole) of sodium hydride (60% in mineral oil) in 20 mL of toluene is stirred, and a solution of 24.3 grams (0.080 mole) of [(1,4-dioxaspiro[4.5]decan-8-yl)(3-trifluoromethylphenyl)] methanol in 65 mL of toluene is added dropwise. Upon completion of addition, the reaction mixture is stirred at ambient temperature for about one hour. After this time a solution of 13.7 grams (0.080 mole) of phenylmethyl bromide in 45 mL of toluene is added dropwise. Upon completion of addition, the reaction mixture is heated to reflux where it is stirred for about 4 hours. The reaction mixture is then cooled and shaken with water. The organic layer is separated and dried with magnesium sulfate. The mixture is filtered and the filtrate is concentrated under reduced pressure, yielding phenylmethyl [(1,4-dioxaspiro[4.5] decan-8-yl)(3-trifluoromethylphenyl)]methyl ether.

Step E Synthesis of phenylmethyl [(cyclohexanon-4-yl)(3-trifluoromethylphenyl)]methyl ether as an intermediate This compound is prepared in a manner analogous to that of Step D of Example 2, using 20.3 grams (0.050 mole) of phenylmethyl [(1,4-dioxaspiro-[4.5]decan-8-yl)(3-trifluoromethylphenyl)]methyl ether and 35 mL of water in 125 mL of acetic acid, yielding phenylmethyl [(cyclohexanon-4-yl)(3-trifluoromethylphenyl)]methyl ether.

Step F Synthesis of 2,4-diamino-6-[(phenylmethoxy)(3-trifluoromethylphenyl)methyl]-5,6,7,8-tetrahydroquinazoline as an intermediate This compound is prepared in a manner analogous to that of Example 1, using 4.7 grams (0.013 mole) of phenylmethyl [(cyclohexanon-4-yl)(3-trifluoromethylphenyl)]methyl ether and 1.2 grams (0.01 4 mole) of cyanoguanidine in 2-(2-ethoxyethoxy)ethanol, yielding 2,4-diamino-6-[(phenylmethoxy)(3-trifluoromethylphenyl)methyl]-5,6,7,8-tetrahydroquinazoline.

Step G Synthesis of [(2,4-diamino-5,6,7,8-tetrahydroquinazolin-6-yl)(3-trifluoromethylphenyl)]methanol as an intermediate A mixture of 4.3 grams (0.010 mole) of 2,4-diamino-6-[(phenylmethoxy)(3-trifluoromethylphenyl)]methyl-5,6,7,8-tetrahydroquinazoline and a catalytic amount of 5% palladium on charcoal in 30 mL of ethanol is hydrogenated using a Parr hydrogenator. Upon completion of the uptake of the theoretical amount of hydrogen, the reaction mixture is filtered. The filtrate is concentrated under reduced pressure, yielding [(2,4-diamino-5,6,7,8-tetrahydroquinazolin-6-yl)(3-trifluoromethylphenyl)]methanol Step H Synthesis of 2,4-diamino-6-(3-trifluortrimethylphenyl)carbonyl-5,6,7,8-tetrahydroquinazoline (Compound 174)

A stirring solution of 1.4 grams (0.011 mole) of oxalyl chloride in 25 mL of methylene chloride is cooled to –60° C., and a solution of 1.9 grams (0.024 mole) of dimethyl sulfoxide in 5 mL of methylene chloride is added dropwise during a five minute period. Upon completion of addition, the reaction mixture is stirred at –60° C. for about 10 minutes, then a solution of 3.4 grams (0.010 mole) of [(2,4-diamino-5,6,7,8-tetrahydroquinazolin-6-yl)(3-trifluoromethylphenyl)]methanol in 5 mL of methylene chloride is added dropwise during a five minute period. Upon completion of addition, the reaction mixture is stirred for 15 minutes, and 5.1 grams (0.050 mole) of triethylamine is added while maintaining the reaction mixture temperature at –60° C. Upon completion of addition, the reaction mixture is allowed to warm to ambient temperature, and 30 mL of water is added. The mixture is stirred for 10 minutes, and the organic layer is separated. The aqueous layer is washed with 20 mL of methylene chloride. The methylene chloride wash and the organic layer are combined, and the combination is washed with 10 mL of water and then with 10 mL of an aqueous solution saturated with sodium chloride. The organic layer is dried with magnesium sulfate and filtered. The filtrate is concentrated under reduced pressure, yielding 2,4-diamino-6-(3-trifluoromethylphenyl)carbonyl-5,6,7,8-tetrahydroquinazoline.

NOTE: The procedure to prepare 2,4-diamino-6-(3-trifluoromethylphenyl)carbonyl-5,6,7,8-tetrahydroquinazoline as shown in Step H above is disclosed by D. Swern et al., Tetrahedron, 34, 1651–1660 (1978)

EXAMPLE 10

SYNTHESIS OF 2,4-DIAMINO-6-(3-TRIFLUOROMETHYLPHENOXY)-5,6,7,8-TETRAHYDROQUINAZOLINE
(COMPOUND 152)

Step A Synthesis of 8-(3-trifluoromethylphenoxy)-1,4-dioxaspiro[4.5]decane as an intermediate A mixture of 4.5 grams (0.028 mole) of 3-trifluoromethylphenol and 1.1 grams (0.028 mole) of sodium hydride (60% in mineral oil) in 100 mL of toluene is stirred at ambient temperature for about 20 minutes, and a solution of 6.6 grams (0.028 mole) of 8-methylsulfonyloxy-1,4-dioxaspiro[4.5]decane (prepared as in Step C of Example 8) in 20 mL of toluene is added dropwise. Upon complete addition, the reaction mixture is heated to reflux where it is stirred for about four hours. The reaction mixture is cooled and concentrated under reduced pressure, yielding 8-(3-trifluoromethylphenoxy)-1,4-dioxaspiro[4.5]decane.

Step B Synthesis of 4-(3-trifluoromethylphenoxy)cyclohexanone as an intermediate This compound was prepared in a manner analogous to that of Step D of Example 2, using 7.6 grams (0.025 mole) of 8-(3-trifluoromethylphenoxy)-1,4-dioxaspiro[4.5]decane and 25 mL of water in 50 mL of acetic acid, yielding 4-(3-trifluoromethylphenoxy)cyclohexanone.

Step C Synthesis of 2,4-diamino-6-(3-trifluoromethylphenoxy)-5,6,7,8-tetrahydroquinazoline (Compound 152)

This compound is prepared in a manner analogous to that of Example 1, using 3.4 grams (0.013 mole) of 4-(3-trifluoromethylphenoxy)cyclohexanone and 1.2 grams (0.014 mole) of cyanoguanidine in 2-(2-ethoxyethoxy)ethanol, yielding 2,4-diamino-6-(3-trifluoromethylphenoxy)-5,6,7,8-tetrahydroquinazoline.

EXAMPLE 11

SYNTHESIS OF 2,4-DIAMINO-6-(3-TRIFLUOROMETHYLPHENYLMETHOXY)-5,6,7,8-TETRAHYDROQUINAZOLINE
(COMPOUND 163)

Step A Synthesis of 8-(3-trifluoromethylphenylmethoxy)-1,4-dioxaspiro[4.5]decane as an intermediate This compound is prepared in a manner analogous to that of Step D of Example 9, using 4.7 grams (0.030 mole) of 1,4-dioxaspiro[4.5]decan-8-ol (prepared as in Step B of Example 8), 7.2 grams (0.030 mole) of 3-trifluoromethylphenylmethyl bromide, and 1.3 grams (0.033 mole) of sodium hydride (60% in mineral oil) in 60 mL of toluene, yielding 8-(3-trifluoromethyl phenyl methoxy)-1,4-dioxaspiro[4.5]decane.

Step B Synthesis of 4-(3-trifluoromethylphenylmethoxy)cyclohexanone as an intermediate This compound is prepared in a manner analogous to that of Step D of Example 2, using 7.9 grams (0.025 mole) of 8-(3-trifluoromethylphenylmethoxy)-1,4-dioxaspiro[4.5]decane, and 25 mL of water in 50 mL of acetic acid, yielding 4-(3-trifluoromethylphenylmethoxy)cyclohexanone.

Step C Synthesis of 2,4-diamino-6-(3-trifluoromethylphenylmethoxy)-5,6,7,8-tetrahydroquinazoline (Compound 163)

This compound is prepared in a manner analogous to that of Example 1, using 3.5 grams (0.013 mole) of 4-(3-trifluoromethylphenoxy)cyclohexanone and 1.2 grams (0.014 mole) of cyanoguanidine in 2-(2-ethoxyethoxy)ethanol, yielding 2,4-diamino-6-(3-trifluoromethylphenylmethoxy)-5,6,7,8-tetrahydroquinazoline.

EXAMPLE 12

SYNTHESIS OF 2,4-DIAMINO-6-(3,5-DICHLOROPHENOXYIMINO)-5,6,7,8-TETRAHYDROQUINAZOLINE
(COMPOUND 184)

Step A Synthesis of 2,4-diamino-5,6,7,8-tetrahydroquinazoline 6-ethylene ketal (Compound 8) as an intermediate This compound was prepared in a manner analogous to that of Example 1, using 25.0 grams (0.16 mole) of 1,4-cyclohexanedione monoethylene ketal and 9.0 grams (0.11 mole) of cyanoguanidine in 100 mL of 2-(2-ethoxyethoxy) ethanol, yielding about 10.5 grams of 2,4-diamino-5,6,7,8-tetrahydroquinazoline 6-ethylene ketal, mp 240°-242° C. The NMR spectrum was consistent with the proposed structure.

Step B Synthesis of 2,4-di[(1,1-dimethylethyl) carbonylamino]-5,6,7,8-tetrahydroquinazoline 6-ethylene ketal as an intermediate A stirred mixture of 24.4 grams (0.11 mole) of 2,4-diamino-5,6,7,8-tetrahydroquinazoline 6-ethylene ketal and 0.5 gram (catalyst) of 4-dimethylaminopyridine in 67 mL (0.33 mole) of pivalic anhydride is heated at reflux for about two hours. The mixture is cooled and poured into 300 mL of water. The mixture is extracted with several portions of ethyl acetate. The combined extracts are washed with water and then dried with magnesium sulfate. The mixture is filtered, and the filtrate is concentrated under reduced pressure, yielding 2,4-di[(1,1-dimethylethyl)carbonylamino]-5,6,7,8-tetrahydroquinazoline 6-ethylene ketal.

Step C Synthesis of 2,4-di[(1,1-dimethylethyl) carbonylamino]-5,6,7,8-tetrahydro-6-quinazolinone as an intermediate This compound was prepared in a manner analogous to that of Step D of Example 2, using 9.8 grams (0.025 mole) of 2,4-di[(1,1-dimethylethyl)carbonylamino]-5,6,7,8-tetrahydroquinazoline 6-ethylene ketal and 25 mL of water in 50 mL of acetic acid, yielding 2,4-di[(1,1-dimethylethyl) carbonylamino]-5,6,7,8-tetrahydro-6-quinazolinone.

Step D Synthesis of O-(3,5-dichlorophenyl)hydroxylamine as an intermediate

Sodium hydride (50% in mineral oil), 4.0 grams (0.084 mole), is placed in a reaction vessel and washed with three portions of hexane. The sodium hydride is then stirred with 30 mL of N,N-dimethylformamide, and a solution of 13.7 grams (0.084 mole) of 3,5-dichlorophenol in 45 mL of N,N-dimethylformamide is added dropwise. Upon completion of addition, the reaction mixture is warmed to 70°-90° C. where it is stirred for about 45 minutes. After this time the reaction mixture is cooled to about 2° C., and 13.4 grams (0.068 mole) of O-(2,4-dinitrophenyl)hydroxylamine [prepared by the method of T. Sheradsky et al., Tetrahedron, 28, 3833 (1972)] is added in one portion. Upon completion of addition, the reaction mixture is stirred at about 2° C. for 10 minutes. The cooling medium is then removed, and the reaction mixture is allowed to warm to ambient temperature where it is stirred for about 3.5 hours. After this time the reaction mixture is poured into about 1000 mL of ice-water. The resultant precipitate is collected by filtration and washed with water. The solid is dried and then is dissolved in ethyl acetate. The solution is then washed, in turn, with one 60 mL portion of aqueous 5% sodium hydroxide, one 150 mL portion of water, one 60 mL portion of aqueous 5% sodium hydroxide, two 300 mL portions of water, and one 100 mL portion of an aqueous solution saturated with sodium chloride. The organic layer is dried with sodium sulfate and filtered. The filtrate is concentrated under reduced pressure, yielding O-(3,5-dichlorophenyl)hydroxylamine.

Step E Synthesis of 2,4-di[(1,1-dimethylethyl) carbonylamino]-6-(3,5-dichlorophenoxyimino)-5,6,7,8-tetrahydroquinazoline as an intermediate A solution of 3.5 grams (0.010 mole) of 2,4-di[(1,1-dimethylethyl)carbonylamino]-5,6,7,8-tetrahydro-6-quinazolinone (prepared in Step C of this Example) in 30 mL of ethanol is stirred, and a solution of 2.1 grams (0.012 mole) of O-(3,5-dichlorophenyl)hydroxylamine in 15 mL of ethanol is added dropwise. Upon completion of addition, the reaction mixture is heated to reflux, where it is stirred for about four hours. After this time the reaction mixture is cooled and concentrated under reduced pressure to a residue. The residue is dissolved in diethyl ether and washed with two portions of an aqueous solution saturated with sodium chloride. The organic layer is dried with sodium sulfate and filtered. The filtrate is concentrated under reduced pressure, yielding 2,4-di[(1,1-dimethylethyl)carbonylamino]-6-(3,5-dichlorophenoxyimino)-5,6,7,8-tetrahydroquinazoline.

Step F Synthesis of 2,4-diamino-6-(3,5-dichlorophenoxyimino)-5,6,7,8-tetrahydroquinazoline (Compound 184)

A suspension of 2.5 grams (0.005 mole) of 2,4-di[(1,1-dimethylethyl)carbonylamino]-6-(3,5-dichlorophenoxyimino)-5,6,7,8-tetrahydroquinazoline in 40 mL of tetrahydrofuran is stirred, and a methanolic solution saturated with hydrogen chloride is added portionwise until a clear solution is obtained. After this time about 2 mL of water is added, and the reaction mixture is heated to reflux where it is stirred for about 4 hours. The reaction mixture is then cooled to ambient temperature and is washed with acetone. The reaction mixture is concentrated under reduced pressure, yielding 2,4-diamino-6-(3,5-dichlorophenoxyimino)-5,6,7,8-tetrahydroquinazoline.

EXAMPLE 13

SYNTHESIS OF 2,4-DIAMINO-6-(3-TRIFLUOROMETHYLPHENYLMETHOXYIMINO)-5,6,7,8-TETRAHYDROQUINAZOLINE (COMPOUND 196)

Step A Synthesis of N-(3-trifluoromethylphenylmethoxy) phthalimide as an intermediate A solution of 8.0 grams (0.049 mole) of N-hydroxyphthalimide and 4.0 grams (0.059 mole) of sodium acetate in about 25 mL of dimethyl sulfoxide was stirred, and a solution of 11.5 grams (0.059 mole) of 3-trifluoromethylphenylmethyl chloride in about 15 mL of dimethyl sulfoxide was added dropwise during a 10 minute period. Upon completion of addition, the reaction mixture was heated to about 60° C. where it stirred until there was no apparent color change in the reaction mixture. The reaction mixture was then poured into an ice-water mixture. The resultant solid was collected and washed with water. The solid was then recrystallized with 100 mL of ethanol. The solid was collected by filtration and dried, yielding 12.2 grams of N-(3-trifluoromethylphenylmethoxy)phthalimide, mp 106°-108° C. The NMR spectrum was consistent with the proposed structure.

Step B Synthesis of O-(3-trifluoromethylphenylmethyl) hydroxylamine hydrochloride as an intermediate A suspension of 10.7 grams (0.033 mole) of N-(3-trifluoromethylphenylmethoxy)phthalimide in 40 mL of ethanol was stirred, and a solution of 2.5 grams (0.050 mole) of hydrazine monohydrate in 10 mL of ethanol was added dropwise. Upon completion of addition, the reaction mixture was stirred at ambient temperature for about 1.5 hours, during which time a voluminous precipitate formed. The reaction mixture was filtered, and the filter cake was washed with ethanol. The combined filtrate and wash was acidified with concentrated hydrochloric acid. The acidic solution was concentrated under reduced pressure, and the residue was triturated with diethyl ether. The resulting solid was collected by filtration and washed with diethyl ether, yielding, when dried: 6.5 grams of O-(3- trifluoromethylphenylmethyl)hydroxylamine hydrochloride, mp 170°–175° C., dec. The NMR spectrum was consistent with the proposed structure.

Step C Synthesis of 2,4-di[(1,1-dimethylethyl) carbonylamino]-6-(3-trifluoromethylphenylmethoxyimino)-5,6,7,8-tetrahydroquinazoline as an intermediate This compound is prepared in a manner analogous to that of Step E of Example 12, using 3.5 grams (0.010 mole) of 2,4-di[(1,1-dimethylethyl)carbonylamino]-5,6,7,8-tetrahydro-6-quinazolinone (prepared in Step C of Example 12) and 2.7 grams (0.012 mole) of O-(3-trifluoromethylphenylmethyl)hydroxylamine hydrochloride in about 45 mL of ethanol. This preparation differs from Step E of Example 12 in that prior to heating at reflux for four hours, 1.5 grams (0.01 5 mole) of triethylamine is added as an acid acceptor, yielding 2,4-di[(1,1-dimethylethyl) carbonylamino]-6-(3-trifluoromethylphenylmethoxyimino)-5,6,7,8-tetrahydroquinazoline.

Step D Synthesis of 2,4-diamino-6-(3-trifluoromethylphenylmethoxyimino)-5,6,7,8-tetrahydroquinazoline (Compound 196)

This compound is prepared in a manner analogous to that of Step F of Example 12, using 2.6 grams (0.005 mole) of 2,4-di[(1,1-dimethylethyl)carbonylamino]-6-(3-trifluoromethylphenylmethoxyimino)-5,6,7,8-tetrahydroquinazoline and a methanolic solution saturated with hydrogen chloride in about 40 mL of tetrahydrofuran, yielding 2,4-diamino-6-(3-trifluoromethylphenylmethoxyimino)-5,6,7,8-tetrahydroquinazoline.

EXAMPLE 14

SYNTHESIS OF 2,4-DIAMINO-6-(PHENYLDIMETHYLSILYL)-5,6,7,8-TETRAHYDROQUINAZOLINE (COMPOUND 204)

Step A Synthesis of 8-phenyldimethylsilyl-1,4-dioxaspiro[4.5]decane as an intermediate This compound is prepared in a manner analogous to that of Step B of Example 6 and Step C of Example 9, using 22.1 grams (0.09 mole) of the Grignard reagent of 8-bromo-1,4-dioxaspiro[4.5]decane (prepared in Step B of Example 9) and 17.1 grams (0.10 mole) of chlorodimethylphenylsilane. Upon completion of the reaction, the reaction mixture is poured into a mixture of 100 grams of ice, 100 mL of an aqueous solution saturated with ammonium chloride, and 200 mL of diethyl ether. This mixture is filtered, and the organic layer is separated. The organic layer is concentrated under reduced pressure, yielding 8-phenyldimethylsilyl-1,4-dioxaspiro[4.5]decane.

Step B Synthesis 4-(phenyldimethylsilyl)cyclohexanone as an intermediate

This compound was prepared in a manner analogous to that of Step D of Example 2, using 13.8 grams (0.050 mole) of 8-phenyldimethylsilyl-1,4-dioxa-spiro[4.5]decane and 25 mL of water in 50 mL of acetic acid, yielding 4-(phenyldimethylsilyl)cyclohexanone.

Step C Synthesis of 2,4-diamino-6-(dimethylphenylsilyl)-5,6,7,8-tetrahydroquinazoline (Compound 204)

This compound is prepared in a manner analogous to that of Example 1, using 3.0 grams (0.013 mole) of 4-(phenyldimethylsilyl)cyclohexanone and 1.2 grams (0.014 mole) of cyanoguanidine in 2-(2-ethoxyethoxy) ethanol, yielding 2,4-diamino-6-(phenyldimethylsilyl)-5,6,7,8-tetrahydroquinazoline.

EXAMPLE 15

SYNTHESIS OF AN ISOMERIC MIXTURE OF CIS/TRANS-2,4-DIAMINO-5-METHYL6-PHENYL-5,6,7,8-TETRAHYDROQUINAZOLINE (COMPOUND 216) AND CIS/TRANS-2,4-DIAMINO-7-METHYL-6-PHENYL-5,6,7,8-TETRAHYDROQUINAZOLINE (COMPOUND 215)

Step A Synthesis of 4-phenyl-2-cyclohexenone as an intermediate

Under a nitrogen atmosphere, a solution of 11.0 grams (0.063 mole) of 4-phenylcyclohexanone in 400 mL of ethyl acetate was stirred, and 14.5 grams (0.076 mole) of phenylselenenyl chloride was added in one portion. The reaction mixture was stirred for one hour and then was washed with three 100 mL portions of water. Tetrahydrofuran, 200 mL, was added, and the reaction mixture was cooled in an ice-bath. The reaction mixture was stirred, and 18.1 mL (0.160 mole) of aqueous 30% hydrogen peroxide was added at a rate to maintain the reaction mixture temperature below 35° C. Upon completion of addition, the reaction mixture was allowed to warm to ambient temperature, where it was stirred for about one hour. The reaction mixture was then washed with one 100 mL portion of water and two 50 mL portions of aqueous 20% sodium carbonate. The organic layer was dried with magnesium sulfate and filtered. The filtrate was concentrated under reduced pressure to a residue. The residue was subjected to column chromatography on silica gel. Elution was accomplished commencing with 10% diethyl ether in petroleum ether and finishing with 20% diethyl ether in petroleum ether. The product-containing fractions were combined and concentrated under reduced pressure, yielding 4.6 grams of 85% pure 4-phenyl-2-cyclohexenone. The NMR spectrum was consistent with the proposed structure. This reaction was repeated on a larger scale.

Step B Synthesis of 3-methyl-4-phenylcyclohexanone as an intermediate

Under a nitrogen atmosphere, a stirred mixture of 2.9 grams (0.020 mole) of copper(I) bromide in 10 mL of diethyl ether was cooled to −20° C., and 50 mL (0.070 mole) of 1.4M methyllithium in diethyl ether was added slowly. Upon completion of addition, a solution of 4.6 grams (0.027 mole) of 4-phenyl-2-cyclohexenone in 5 mL of diethyl ether was added dropwise at a rate to maintain the reaction mixture temperature below −20° C. Upon completion of addition, a solution of 4.2 grams (0.080 mole) of ammonium chloride in 20 mL of water was added. Upon completion of addition, the reaction mixture was stirred as it warmed to ambient temperature. The reaction mixture was then diluted with 200 mL of diethyl ether and filtered. The filtrate was concentrated under reduced pressure to a residue. The residue was subjected to column chromatography on silica gel. Elution was accomplished commencing with 10% diethyl ether in petroleum ether and finishing with 15% diethyl ether in petroleum ether. The product-containing fractions were combined and concentrated under reduced pressure, yielding 1.9 grams of 3-methyl-4-phenylcyclohexanone as a liquid. The NMR spectrum was consistent with the proposed structure, and it indicated that the product was predominantly the trans isomer. The reaction-was repeated on a larger scale. The 3-methyl-4-phenylcyclohexanone isolated from the larger reaction was a solid, mp 71.5°–72.5° C. The NMR spectrum of a sample from the larger reaction was also consistent with the proposed structure.

Step C Synthesis of an isomeric mixture of cis/trans-2,4-diamino-5-methyl-6-phenyl-5,6,7,8-tetrahydroquinazoline (Compound 216) and cis/trans-2,4-diamino-7-methyl-6-phenyl-5,6,7,8-tetrahydroquinazoline (Compound 215)

The mixture of these isomers was prepared in a manner analogous to that of Example 1, using 7.0 grams (0.037 mole) of 3-methyl-4-phenylcyclohexanone and 3.4 grams (0.040 mole) of cyanoguanidine in ethoxyethoxy) ethanoethoxyethoxy)ethanol, yielding 1.3 grams of diamino-5-methyl-6-phenyl-5,6,7,8-tetrahydroquinazoline and cis/trans-2,4-diamino-7-methyl-6-phenyl-5,6,7,8-tetrahydroquinazoline. The NMR spectrum was consistent with the proposed structures. The cis/trans -2,4-diamino-5-methyl-6-phenyl-5,6,7,8-tetrahydroquinazoline is separated from cis/trans-2,4-diamino-7-methyl-6-phenyl-5,6,7,8-tetrahydroquinazoline by reverse phase high pressure liquid chromatography. The cis and trans geometric isomers of 2,4-diamino-5-methyl-6-phenyl-5,6,7,8-tetrahydroquinazoline and the cis and trans geometric isomers of 2,4-diamino-7-methyl-6-phenyl-5,6,7,8-tetrahydroquinazoline are also separated by reverse phase high pressure liquid chromatography.

EXAMPLE 16

SYNTHESIS OF 4-AMINO-2-METHYLTHIO-6-(2-CHLOROPHENYL)-5,6,7,8-TETRAHYDROQUINAZOLINE (COMPOUND 228)

Step A Synthesis of 1-(2-chlorophenyl)-1-cyclohexen-4-one as an intermediate

This compound is prepared in a manner analogous to that of Step D of Example 7, using 9.5 grams (0.040 mole) of 1-chloro-2-iodobenzene, 1.1 grams (0.044 mole) of magnesium turnings, 6.2 grams (0.040 mole) of 1,4-cyclohexanedione mono-ethylene ketal, and about 1 00 mL of aqueous 10% hydrochloric acid in about 95 mL of tetrahydrofuran, yielding 1-(2-chlorophenyl)-1-cyclohexen-4-one.

Step B Synthesis of 4-(2-chlorophenyl)cyclohexanone as an intermediate

This compound is prepared in a manner analogous to that of Step C of Example 2 by the hydrogenation of 6.5 grams (0.026 mole) of 1-(2-chlorophenyl)-1-cyclohexen-4-one in the presence of 0.4 gram (catalyst) of 10% palladium on charcoal in 50 mL of ethanol, yielding 4-(2-chlorophenyl) cyclohexanone.

Step C Synthesis of 4-amino-2-methylthio-6-(2-chlorophenyl)-5,6,7,8-tetrahydroquinazoline (Compound 234)

A suspension of 1.2 grams of (0.010 mole) of N-cyano-S-methylisothiourea [prepared in the manner disclosed by R. W. Turner; Synthesis, 332 (1975)], 2.1 grams (0.010 mole) of 4-(2-chlorophenyl)cyclohexanone and 0.4 gram (0.005 mole) of pyrrolidine is placed in a glass tube, which is then sealed. The sealed tube is heated at 150° C. for about seven hours. After this time, the sealed tube is cooled in an ice-bath and opened. The reaction mixture is concentrated under reduced pressure to a residue. The residue is subjected to column chromatography using silica gel, yielding 4-amino-2-methylthio-6-(2-chlorophenyl)-5,6,7,8-tetrahydroquinazoline.

EXAMPLE 17

SYNTHESIS OF 4-AMINO-2-METHYLSULFINYL-6-(2-CHLOROPHENYL)-5,6,7,8-TETRAHYDROQUINAZOLINE (COMPOUND 231)

A stirred solution of 1.5 grams (0.005 mole) of 4-amino-2-methylthio-6-(2-chlorophenyl)-5,6,7,8-tetrahydroquinazoline (prepared as in Example 16) in 20 mL of chloroform is cooled to −10° C., and a solution of 1.7 grams (0.005 mole) of 50–60% 3-chloroperoxybenzoic acid in 30 mL of chloroform is added dropwise at a rate to maintain the reaction mixture temperature at −10° C. Upon completion of addition, the reaction mixture is maintained at −10° C. for one hour. After this time the reaction mixture is allowed to warm to ambient temperature, where it stands for about 18 hours. The reaction mixture is then washed with an aqueous 10% solution of potassium carbonate. The organic layer is dried with magnesium sulfate and filtered. The filtrate is concentrated under reduced pressure to a residue. The residue is subjected to column chromatography on silica gel, yielding 4-amino-2-methylsulfinyl-6-(2-chlorophenyl)-5,6,7,8-tetrahydroquinazoline.

EXAMPLE 18

SYNTHESIS OF 4-AMINO-2-METHYLAMINO-6-(2-CHLOROPHENYL)-5,6,7,8-TETRAHYDROQUINAZOLINE (COMPOUND 234)

A suspension of 1.6 grams (0.005 mole) of 4-amino-2-methylsulfinyl-6-(2-chlorophenyl)-5,6,7,8-tetrahydroquinazoline (prepared as in Example 17) and 10 mL of aqueous 40% methylamine in 50 mL of ethanol is placed in a glass tube, which is then sealed. The sealed tube is heated at about 180° C. for 7 hours and then is cooled in an ice-bath and opened. The reaction mixture is concentrated under reduced pressure to a residue. The residue is stirred with an aqueous 10% potassium carbonate solution, and the resultant suspension is extracted with chloroform. The extract is dried with magnesium sulfate and filtered. The filtrate is concentrated under reduced pressure to a residue. The residue is subjected to column chromatography on silica gel, yielding 4-amino-2-methylamino-6-(2-chlorophenyl)-5,6,7,8-tetrahydroquinazoline.

EXAMPLE 19

SYNTHESIS OF 4-AMINO-2-(PYRROLIDIN-1-YL)-6-(2-CHLOROPHENYL)-5,6,7,8-TETRAHYDROQUINAZOLINE (COMPOUND 240)

This compound is prepared in a manner analogous to that of Example 18, using 1.60 grams (0.005 mole) of 4-amino-2-methylsulfinyl-6-(2-chlorophenyl)-5,6,7,8-tetrahydroquinazoline (prepared as in Example 17) and 0.71 gram (0.010 mole) of pyrrolidine in 50 mL of isoamyl alcohol. The sealed tube is heated at about 200° C. for 7 hours. The reaction mixture is subjected to column chromatography on silica gel, yielding 4-amino-2-(pyrrolidin-1-yl)-6-(2-chlorophenyl)-5,6,7,8-tetrahydroquinazoline.

EXAMPLE 20

SYNTHESIS OF 2,4-DIAMINO-6-(2,3-DIHYDRO-2,2-DIMETHYLBENZOFURAN-5-YL)-5,6,7,8-TETRAHYDROQUINAZOLINE (COMPOUND 250)

Step A Synthesis of 1-(2,3-dihydro-2,2-dimethylbenzofuran-5-yl)-1-cyclohexen-4-one as an intermediate This compound is prepared in a manner analogous to that of Step D of Example 7, using 9.2 grams (0.040 mole) of 5-bromo-2,3-dihydro-2,2-dimethylbenzofuran, 1.1 grams (0.044 mole) of magnesium turnings, and 6.2 grams (0.040 mole) of 1,4-cyclohexanedione mono-ethylene ketal in about 70 mL of tetrahydrofuran, yielding 1-(2,3-dihydro-2,2-dimethylbenzofuran-5-yl)-1-cyclohexen-4-one.

Step B Synthesis of 4-(2,3-dihydro-2,2-dimethylbenzofuran-5-yl)-1-cyclohexanone as an intermediate This compound is prepared in a manner analogous to that of Step C of Example 2, by the hydrogenation of 6.3 grams (0.026 mole) of 1-(2,3-dihydro-2,2-dimethylbenzofuran-5-yl)-1-cyclohexen-4-one in the presence of 0.4 gram (catalyst) of 10% palladium on charcoal in 50 mL of ethanol, yielding 4-(2,3-dihydro-2,2-dimethylbenzofuran-5-yl)-1-cyclohexanone.

Step C Synthesis of 2,4-diamino-6-(2,3-dihydro-2,2-dimethylbenzofuran-5-yl)-5,6,7,8-tetrahydroquinazoline (Compound 250)

This compound is prepared in a manner analogous to that of Example 1, using 3.2 grams (0.013 mole) of 4-(2,3-dihydro-2,2-dimethylbenzofuran-5-yl)-1-cyclohexanone and 1.2 grams (0.014 mole) of cyanoguanidine in 2-(2-ethoxyethoxy)ethanol, yielding 2,4-diamino-6-(2,3-dihydro-2,2-dimethylbenzofuran-5-yl)-5,6,7,8-tetrahydroquinazoline.

TABLE 1

SUBSTITUTED 2,4-DIAMINO-5,6,7,8-TETRAHYDROQUINAZOLINES AS INSECTICIDES

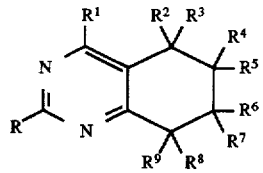

Where R and $R^1$ are amino; and $R^2$, $R^3$, $R^6$, $R^7$, $R^8$ and $R^9$ are hydrogen

| Cmpd. No. | $R^4$ | $R^5$ |
|---|---|---|
| 1 | H | H |
| 2 | —$CH_3$ | H |
| 3 | —$C_3H_7$ | H |
| 4 | —$C(CH_3)_3$ | H |
| 5 | —$C_9H_{19}$ | H |
| 6 | cyclohexyl | H |
| 7 | —$CH(CH_3)C_3H_7$ | H |
| 8 | —$OCH_2CH_2O$— | |

Wherein R and $R^1$ are amino; $R^2$, $R^3$, $R^5$, $R^6$, $R^7$, $R^8$ and $R^9$ are hydrogen; and $R^4$ is -$(n)_m$-$R^{10}$, where $R^{10}$ is

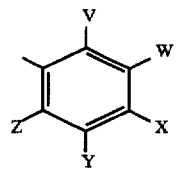

| Cmpd. No. | m | n | V | W | X | Y | Z |
|---|---|---|---|---|---|---|---|
| 9 | 0 | — | H | H | H | H | H |
| 10 | 0 | — | Cl | H | H | H | H |
| 11 | 0 | — | H | Cl | H | H | H |
| 12 | 0 | — | H | H | Cl | H | H |
| 13 | 0 | — | H | H | F | H | H |
| 14 | 0 | — | Cl | Cl | H | H | H |
| 15 | 0 | — | H | Cl | Cl | H | H |
| 16 | 0 | — | H | Cl | H | Cl | H |
| 17 | 0 | — | F | H | F | H | H |
| 18 | 0 | — | F | H | F | H | F |
| 19 | 0 | — | —$CH_3$ | H | H | H | H |
| 20 | 0 | — | H | H | —$CH_3$ | H | H |
| 21 | 0 | — | H | —$CH_3$ | H | —$CH_3$ | H |
| 22 | 0 | — | —$CF_3$ | H | H | H | H |
| 23 | 0 | — | H | —$CF_3$ | H | H | H |
| 24 | 0 | — | H | H | —$CF_3$ | H | H |
| 25 | 0 | — | H | —$CF_3$ | H | —$CF_3$ | H |
| 26 | 0 | — | —CN | H | H | H | H |
| 27 | 0 | — | —$CO_2CH_3$ | H | H | H | H |
| 28 | 0 | — | H | —$CO_2CH_3$ | H | H | H |
| 29 | 0 | — | H | —$CO_2CH_3$ | H | Cl | H |
| 30 | 0 | — | H | —$CO_2CH_3$ | H | —$CF_3$ | H |

TABLE 1-continued

| # | | | | | | | |
|---|---|---|---|---|---|---|---|
| 31 | 0 | — | H | H | methoxyphenyl | H | H |
| 32 | 0 | — | —CH=CHCH=CH— | | H | H | H |
| 33 | 0 | — | H | —CH=CHCH=CH— | | H | H |
| 34 | 0 | — | —OC(CH$_3$)$_2$CH$_2$— | | H | H | H |
| 35 | 0 | — | —OC(CH$_3$)$_2$CH$_2$— | | H | Cl | H |
| 36 | 0 | — | —CH$_2$C(CH$_3$)$_2$O— | | H | H | H |
| 37 | 0 | — | —OCF$_2$CF$_2$— | | H | H | H |
| 38 | 0 | — | —OCF$_2$CF$_2$— | | H | Cl | H |
| 39 | 0 | — | —OCF$_2$CF$_2$— | | H | F | H |
| 40 | 0 | — | —OCF$_2$CF$_2$— | | H | —CF$_3$ | H |
| 41 | 0 | — | —CF$_2$CF$_2$O— | | H | H | H |
| 42 | 0 | — | —CF$_2$CF$_2$O— | | H | Cl | H |
| 43 | 0 | — | —CF$_2$CF$_2$O— | | H | F | H |
| 44 | 0 | — | —CF$_2$CF$_2$O— | | H | —CF$_3$ | H |
| 45 | 0 | — | —OCF$_2$O— | | H | H | H |
| 46 | 0 | — | —OCF$_2$O— | | H | Cl | H |
| 47 | 0 | — | —OCF$_2$O— | | H | F | H |
| 48 | 0 | — | —OCF$_2$O— | | H | —CF$_3$ | H |
| 49 | 0 | — | 4-fluorophenyl | H | H | H | H |
| 50 | 0 | — | 4-(trifluoromethyl)phenyl | H | H | H | H |
| 51 | 0 | — | —CH$_3$ | phenyl | H | H | H |
| 52 | 1 | —CH$_2$— | H | H | H | H | H |
| 53 | 1 | —CH$_2$— | Cl | H | H | H | H |
| 54 | 1 | —CH$_2$— | H | Cl | H | H | H |
| 55 | 1 | —CH$_2$— | H | H | Cl | H | H |
| 56 | 1 | —CH$_2$— | H | H | F | H | H |
| 57 | 1 | —CH$_2$— | Cl | Cl | H | H | H |
| 58 | 1 | —CH$_2$— | H | Cl | Cl | H | H |
| 59 | 1 | —CH$_2$— | H | Cl | H | Cl | H |
| 60 | 1 | —CH$_2$— | F | H | F | H | H |
| 61 | 1 | —CH$_2$— | F | H | F | H | F |
| 62 | 1 | —CH$_2$— | —CH$_3$ | H | H | H | H |
| 63 | 1 | —CH$_2$— | H | H | —CH$_3$ | H | H |
| 64 | 1 | —CH$_2$— | H | —CH$_3$ | H | —CH$_3$ | H |
| 65 | 1 | —CH$_2$— | —CF$_3$ | H | H | H | H |
| 66 | 1 | —CH$_2$— | H | —CF$_3$ | H | H | H |
| 67 | 1 | —CH$_2$— | H | H | —CF$_3$ | H | H |
| 68 | 1 | —CH$_2$— | H | —CF$_3$ | H | —CF$_3$ | H |
| 69 | 1 | —CH$_2$— | —CN | H | H | H | H |
| 70 | 1 | —CH$_2$— | —CO$_2$CH$_3$ | H | H | H | H |
| 71 | 1 | —CH$_2$— | H | —CO$_2$CH$_3$ | H | H | H |
| 72 | 1 | —CH$_2$— | H | —CO$_2$CH$_3$ | H | Cl | H |
| 73 | 1 | —CH$_2$— | H | —CO$_2$CH$_3$ | H | —CF$_3$ | H |
| 74 | 1 | —CH$_2$— | H | H | methoxyphenyl | H | H |
| 75 | 1 | —CH$_2$— | —CH=CHCH=CH— | | H | H | H |
| 76 | 1 | —CH$_2$— | H | —CH=CHCH=CH— | | H | H |
| 77 | 1 | —CH$_2$— | —OC(CH$_3$)$_2$CH$_2$— | | H | H | H |
| 78 | 1 | —CH$_2$— | —OC(CH$_3$)$_2$CH$_2$— | | H | Cl | H |
| 79 | 1 | —CH$_2$— | —CH$_2$C(CH$_3$)$_2$O— | | H | H | H |
| 80 | 1 | —CH$_2$— | —OCF$_2$CF$_2$— | | H | H | H |
| 81 | 1 | —CH$_2$— | —OCF$_2$CF$_2$— | | H | Cl | H |
| 82 | 1 | —CH$_2$— | —OCF$_2$CF$_2$— | | H | F | H |
| 83 | 1 | —CH$_2$— | —OCF$_2$CF$_2$— | | H | —CF$_3$ | H |
| 84 | 1 | —CH$_2$— | —CF$_2$CF$_2$O— | | H | H | H |
| 85 | 1 | —CH$_2$— | —CF$_2$CF$_2$O— | | H | Cl | H |
| 86 | 1 | —CH$_2$— | —CF$_2$CF$_2$O— | | H | F | H |
| 87 | 1 | —CH$_2$— | —CF$_2$CF$_2$O— | | H | —CF$_3$ | H |
| 88 | 1 | —CH$_2$— | —OCF$_2$O— | | H | H | H |
| 89 | 1 | —CH$_2$— | —OCF$_2$O— | | H | Cl | H |

TABLE 1-continued
| | | | | | | | |
|---|---|---|---|---|---|---|---|
| 90 | 1 | —CH₂— | —OCF₂O— | H | F | H | |
| 91 | 1 | —CH₂— | —OCF₂O— | H | —CF₃ | H | |
| 92 | 1 | —CH₂— | 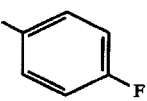 4-F-C₆H₄ | H | H | H | H |
| 93 | 1 | —CH₂— | 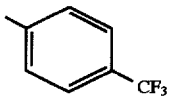 4-CF₃-C₆H₄ | H | H | H | H |
| 94 | 1 | —CH₂— | —CH₃ | phenyl | H | H | H |
| 95 | 1 |  CH(CH₃)₂ | H | H | H | H | H |
| 96 | 1 |  CH(CH₃)₂ | Cl | H | H | H | H |
| 97 | 1 |  CH(CH₃)₂ | H | Cl | H | H | H |
| 98 | 1 |  CH(CH₃)₂ | H | H | Cl | H | H |
| 99 | 1 |  CH(CH₃)₂ | H | H | F | H | H |
| 100 | 1 |  CH(CH₃)₂ | Cl | Cl | H | H | H |
| 101 | 1 |  CH(CH₃)₂ | H | Cl | Cl | H | H |
| 102 | 1 |  CH(CH₃)₂ | H | Cl | H | Cl | H |
| 103 | 1 |  CH(CH₃)₂ | F | H | F | H | H |
| 104 | 1 |  CH(CH₃)₂ | F | H | F | H | F |
| 105 | 1 |  CH(CH₃)₂ | —CH₃ | H | H | H | H |
| 106 | 1 |  CH(CH₃)₂ | H | H | —CH₃ | H | H |
| 107 | 1 |  CH(CH₃)₂ | H | —CH₃ | H | —CH₃ | H |

TABLE 1-continued

| | | | | | | | |
|---|---|---|---|---|---|---|---|
| 108 | 1 | CH(CH₃)₂ | —CF₃ | H | H | H | H |
| 109 | 1 | CH(CH₃)₂ | H | —CF₃ | H | H | H |
| 110 | 1 | CH(CH₃)₂ | H | H | —CF₃ | H | H |
| 111 | 1 | CH(CH₃)₂ | H | —CF₃ | H | —CF₃ | H |
| 112 | 1 | CH(CH₃)₂ | —CN | H | H | H | H |
| 113 | 1 | CH(CH₃)₂ | —CO₂CH₃ | H | H | H | H |
| 114 | 1 | CH(CH₃)₂ | H | —CO₂CH₃ | H | H | H |
| 115 | 1 | CH(CH₃)₂ | H | —CO₂CH₃ | H | Cl | H |
| 116 | 1 | CH(CH₃)₂ | H | —CO₂CH₃ | H | —CF₃ | H |
| 117 | 1 | CH(CH₃)₂ | H | H | OC₆H₅ (methoxyphenyl) | H | H |
| 118 | 1 | CH(CH₃)₂ | —CH=CHCH=CH— | | H | H | H |
| 119 | 1 | CH(CH₃)₂ | H | —CH=CHCH=CH— | | H | H |
| 120 | 1 | CH(CH₃)₂ | —OC(CH₃)₂CH₂— | | H | H | H |
| 121 | 1 | CH(CH₃)₂ | —OC(CH₃)₂CH₂— | | H | Cl | H |
| 122 | 1 | CH(CH₃)₂ | —CH₂C(CH₃)₂O— | | H | H | H |
| 123 | 1 | CH(CH₃)₂ | —OCF₂CF₂— | | H | H | H |

TABLE 1-continued
| | | | | | | | |
|---|---|---|---|---|---|---|---|
| 124 | 1 |  | —OCF$_2$CF$_2$— | | H | Cl | H |
| 125 | 1 |  | —OCF$_2$CF$_2$— | | H | F | H |
| 126 | 1 |  | —OCF$_2$CF$_2$— | | H | —CF$_3$ | H |
| 127 | 1 |  | —CF$_2$CF$_2$O— | | H | H | H |
| 128 | 1 |  | —CF$_2$CF$_2$O— | | H | Cl | H |
| 129 | 1 |  | —CF$_2$CF$_2$O— | | H | F | H |
| 130 | 1 |  | —CF$_2$CF$_2$O— | | H | —CF$_3$ | H |
| 131 | 1 |  | —OCF$_2$O— | | H | H | H |
| 132 | 1 |  | —OCF$_2$O— | | H | Cl | H |
| 133 | 1 |  | —OCF$_2$O— | | H | F | H |
| 134 | 1 |  | —OCF$_2$O— | | H | —CF$_3$ | H |
| 135 | 1 |  | 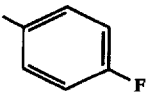 | H | H | H | H |
| 136 | 1 |  | 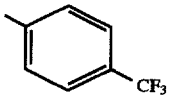 | H | H | H | H |
| 137 | 1 |  | —CH$_3$ | phenyl | H | H | H |
| 138 | 1 |  | H | H | H | H | H |

TABLE 1-continued

| # | | R | | | | | |
|---|---|---|---|---|---|---|---|
| 139 | 1 | 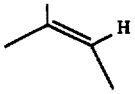 | H | Cl | H | H | H |
| 140 | 1 | 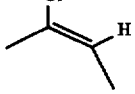 | H | Cl | H | Cl | H |
| 141 | 1 | 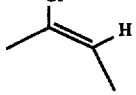 | H | —CF₃ | H | H | H |
| 142 | 1 | 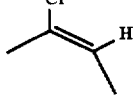 | H | —CF₃ | H | —CF₃ | H |
| 143 | 1 | 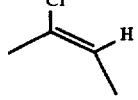 | H | —CO₂CH₃ | H | H | H |
| 144 | 1 | 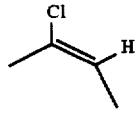 | H | —CO₂CH₃ | H | Cl | H |
| 145 | 1 | 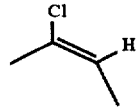 | H | —CO₂CH₃ | H | —CF₃ | H |
| 146 | 1 | 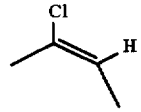 | —CH=CHCH=CH— | | H | H | H |
| 147 | 1 | 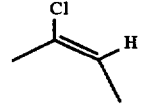 | H | —CH=CHCH=CH— | | H | H |
| 148 | 1 | 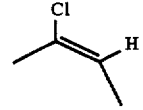 | —OCF₂CF₂— | | H | H | H |
| 149 | 1 | O | H | H | H | H | H |
| 150 | 1 | O | H | Cl | H | H | H |
| 151 | 1 | O | H | Cl | H | Cl | H |
| 152 | 1 | O | H | —CF₃ | H | H | H |
| 153 | 1 | O | H | —CF₃ | H | —CF₃ | H |
| 154 | 1 | O | H | —CO₂CH₃ | H | H | H |
| 155 | 1 | O | H | —CO₂CH₃ | H | Cl | H |
| 156 | 1 | O | H | —CO₂CH₃ | H | —CF₃ | H |
| 157 | 1 | O | —CH=CHCH=CH— | | H | H | H |
| 158 | 1 | O | H | —CH=CHCH=CH— | | H | H |
| 159 | 1 | O | —OCF₂CF₂— | | H | H | H |
| 160 | 1 | —OCH₂— | H | H | H | H | H |
| 161 | 1 | —OCH₂— | H | Cl | H | H | H |
| 162 | 1 | —OCH₂— | H | Cl | H | Cl | H |
| 163 | 1 | —OCH₂— | H | —CF₃ | H | H, | H |
| 164 | 1 | —OCH₂— | H | —CF₃ | H | —CF₃ | H |
| 165 | 1 | —OCH₂— | H | —CO₂CH₃ | H | H | H |
| 166 | 1 | —OCH₂— | H | —CO₂CH₃ | H | Cl | H |

TABLE 1-continued

| | | | | | | | |
|---|---|---|---|---|---|---|---|
| 167 | 1 | —OCH$_2$— | H | —CO$_2$CH$_3$ | H | —CF$_3$ | H |
| 168 | 1 | —OCH$_2$— | —CH=CHCH=CH— | | H | H | H |
| 169 | 1 | —OCH$_2$— | H | —CH=CHCH=CH— | | H | H |
| 170 | 1 | —OCH$_2$— | —OCF$_2$CF$_2$— | | H | H | H |
| 171 | 1 |  | H | H | H | H | H |
| 172 | 1 |  | H | Cl | H | H | H |
| 173 | 1 |  | H | Cl | H | Cl | H |
| 174 | 1 |  | H | —CF$_3$ | H | H | H |
| 175 | 1 |  | H | —CF$_3$ | H | —CF$_3$ | H |
| 176 | 1 |  | H | —CO$_2$CH$_3$ | H | H | H |
| 177 | 1 |  | H | —CO$_2$CH$_3$ | H | Cl | H |
| 178 | 1 |  | H | —CO$_2$CH$_3$ | H | —CF$_3$ | H |
| 179 | 1 |  | —CH=CHCH=CH— | | H | H | H |
| 180 | 1 |  | H | —CH=CHCH=CH— | | H | H |
| 181 | 1 |  | —OCF$_2$CF$_2$— | | H | H | H |
| 182 | 1 | =NO— | H | H | H | H | H |
| 183 | 1 | =NO— | H | Cl | H | H | H |
| 184 | 1 | =NO— | H | Cl | H | Cl | H |
| 185 | 1 | =NO— | H | —CF$_3$ | H | H | H |
| 186 | 1 | =NO— | H | —CF$_3$ | H | —CF$_3$ | H |
| 187 | 1 | =NO— | H | —CO$_2$CH$_3$ | H | H | H |
| 188 | 1 | =NO— | H | —CO$_2$CH$_3$ | H | Cl | H |
| 189 | 1 | =NO— | H | —CO$_2$CH$_3$ | H | —CF$_3$ | H |
| 190 | 1 | =NO— | —CH=CHCH=CH— | | H | H | H |
| 191 | 1 | =NO— | H | —CH=CHCH=CH— | | H | H |
| 192 | 1 | =NO— | —OCF$_2$CF$_2$— | | H | H | H |
| 193 | 1 | =NOCH$_2$— | H | H | H | H | H |
| 194 | 1 | =NOCH$_2$— | H | Cl | H | H | H |
| 195 | 1 | =NOCH$_2$— | H | Cl | H | Cl | H |
| 196 | 1 | =NOCH$_2$— | H | —CF$_3$ | H | H | H |
| 197 | 1 | =NOCH$_2$— | H | —CF$_3$ | H | —CF$_3$ | H |
| 198 | 1 | =NOCH$_2$— | H | —CO$_2$CH$_3$ | H | H | H |
| 199 | 1 | =NOCH$_2$— | H | —CO$_2$CH$_3$ | H | Cl | H |
| 200 | 1 | =NOCH$_2$— | H | —CO$_2$CH$_3$ | H | —CF$_3$ | H |
| 201 | 1 | =NOCH$_2$— | —CH=CHCH=CH— | | H | H | H |
| 202 | 1 | =NOCH$_2$— | H | —CH=CHCH=CH— | | H | H |
| 203 | 1 | =NOCH$_2$— | —OCF$_2$CF$_2$— | | H | H | H |
| 204 | 1 | 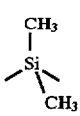 | H | H | H | H | H |

TABLE 1-continued

| | | R² | R³/R⁴ | R⁵ | R⁶ | R⁷ | R⁸ |
|---|---|---|---|---|---|---|---|
| 205 | 1 | CH₃–Si(CH₃)– | H | Cl | H | H | H |
| 206 | 1 | CH₃–Si(CH₃)– | H | Cl | H | Cl | H |
| 207 | 1 | CH₃–Si(CH₃)– | H | –CF₃ | H | H | H |
| 208 | 1 | CH₃–Si(CH₃)– | H | –CF₃ | H | –CF₃ | H |
| 209 | 1 | CH₃–Si(CH₃)– | H | –CO₂CH₃ | H | H | H |
| 210 | 1 | CH₃–Si(CH₃)– | H | –CO₂CH₃ | H | Cl | H |
| 211 | 1 | CH₃–Si(CH₃)– | H | –CO₂CH₃ | H | –CF₃ | H |
| 212 | 1 | CH₃–Si(CH₃)– | –CH=CHCH=CH– | | H | H | H |
| 213 | 1 | CH₃–Si(CH₃)– | H | –CH=CHCH=CH– | | H | H |
| 214 | 1 | CH₃–Si(CH₃)– | –OCF₂CF₂– | | H | H | H |

Wherein R and R¹ are amino; R³, R⁵, R⁷, R⁸ and R⁹ are hydrogen; and R⁴ is -(n)$_m$-R¹⁰, where m is 0, and R¹⁰ is

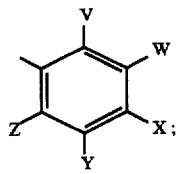

where X and Z are hydrogen.

| Cmpd. No. | R² | R⁶ | V | W | Y |
|---|---|---|---|---|---|
| 215 | H cis/trans | –CH₃ | H | H | H |
| 216 | –CH₃ cis/trans | H | H | H | H |
| 217 | H cis/trans | –CH₃ | Cl | H | H |
| 218 | CH₃ cis/trans | H | Cl | H | H |
| 219 | H | –CH₃ | H | Cl | Cl |

TABLE 1-continued

| | | | | | |
|---|---|---|---|---|---|
| 220 | cis/trans —CH₃ cis/trans | H | H | Cl | Cl |

Wherein R and $R^1$ are amino; $R^3$, $R^5$, $R^7$, $R^8$ and $R^9$ are hydrogen; and $R^4$ is -(n)$_m$-$R^{10}$, where m is 1, n is —CH₂—, and $R^{10}$ is

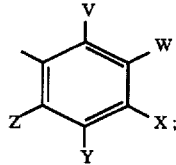

where X and Z are hydrogen.

| Cmpd. No. | $R^2$ | $R^6$ | V | W | Y |
|---|---|---|---|---|---|
| 221 | H | —CH₃ | H | H | H |
| 222 | cis/trans —CH₃ | H | H | H | H |
| 223 | cis/trans H | —CH₃ | Cl | H | H |
| 224 | cis/trans —CH₃ | Cl | H | H | |
| 225 | cis/trans H | —CH₃ | H | Cl | Cl |
| 226 | cis/trans —CH₃ cis/trans | H | H | Cl | Cl |

Wherein $R^1$ is amino; $R^2$, $R^3$, $R^5$, $R^6$, $R^7$, $R^8$ and $R^9$ are hydrogen; and $R^4$ is -(n)$_m$-$R^{10}$, where m is 1, n is —CH₂—, and $R^{10}$ is

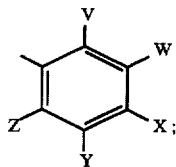

where X and Z are hydrogen.

| Cmpd. No. | R | V | W | Y |
|---|---|---|---|---|
| 227 | —SCH₃ | H | H | H |
| 228 | —SCH₃ | Cl | H | H |
| 229 | —SCH₃ | H | Cl | Cl |
| 230 | —S(O)CH₃ | H | H | H |
| 231 | —S(O)CH₃ | Cl | H | H |
| 232 | —S(O)CH₃ | H | Cl | Cl |

Wherein $R^1$ is amino; R is —$NR^{11}R^{12}$; $R^2$, $R^3$, $R^5$, $R^6$, $R^7$, $R^8$ and $R^9$ are hydrogen; and $R^4$ is -(n)$_m$-$R^{10}$, where m is 1, n is —CH₂—, and $R^{10}$ is

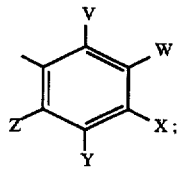

where X and Z are hydrogen.

| Cmpd. No. | $R^{11}$ | $R^{12}$ | V | W | Y |
|---|---|---|---|---|---|
| 233 | H | —CH₃ | H | H | H |
| 234 | H | —CH₃ | Cl | H | H |
| 235 | H | —CH₃ | H | Cl | Cl |
| 236 | —CH₃ | —CH₃ | H | H | H |
| 237 | —CH₃ | —CH₃ | Cl | H | H |
| 238 | —CH₃ | —CH₃ | H | Cl | Cl |
| 239 | —CH₂CH₂CH₂CH₂— | | H | H | H |
| 240 | —CH₂CH₂CH₂CH₂— | | Cl | H | H |
| 241 | —CH₂CH₂CH₂CH₂— | | H | Cl | Cl |
| 242 | —CH₂CH₂CH₂CH₂CH₂— | | H | H | H |

TABLE 1-continued

| | | | | |
|---|---|---|---|---|
| 243 | —CH₂CH₂CH₂CH₂CH₂— | Cl | H | H |
| 244 | —CH₂CH₂CH₂CH₂CH₂— | H | Cl | Cl |
| 245 | —CH₂CH₂OCH₂CH₂— | H | H | H |
| 246 | —CH₂CH₂OCH₂CH₂— | Cl | H | H |
| 247 | —CH₂CH₂OCH₂CH₂— | H | Cl | Cl |

Wherein R and R¹ are amino; R², R³, R⁵, R⁶, R⁷, R⁸ and R⁹ are hydrogen; and R⁴ is -(n)ₘ-R¹⁰, where R¹⁰ is

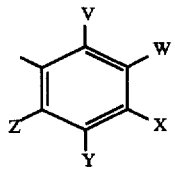

| Cmpd. No. | m | n | V | W | X | Y | Z |
|---|---|---|---|---|---|---|---|
| 248 | 0 | — | Cl | H | Cl | H | H |
| 249 | 0 | — | H | Cl | Cl | H | H |
| 250 | 0 | — | H | —CH₂C(CH₃)₂O— | | H | H |
| 251 | 1 | —CH₂— | Cl | H | Cl | H | H |
| 252 | 1 | —CH₂— | H | Cl | Cl | H | H |
| 253 | 1 | —CH₂— | H | —CH₂C(CH₃)₂O— | | H | |
| 254 | 1 | CH₃-C(CH₃)- | Cl | H | Cl | H | H |
| 255 | 1 | CH₃-C(CH₃)- | H | Cl | Cl | H | H |
| 256 | 1 | CH₃-C(CH₃)- | H | —CH₂C(CH₃)₂O— | | H | H |
| 257 | 0 | — | —OC(CH₃)₂C(=O)— | | H | H | H |
| 258 | 0 | — | —(C(=O)C(CH₃)₂O— | | H | H | H |
| 259 | 0 | — | H | —C(=O)C(CH₃)₂O— | | H | H |
| 260 | 1 | —CH₂— | —OC(CH₃)₂C(=O)— | | H | H | H |
| 261 | 1 | —CH₂— | —C(=O)C(CH₃)₂O— | | H | H | H |
| 262 | 1 | —CH₂— | H | —C(=O)C(CH₃)₂O— | | H | H |
| 263 | 1 | —C(CH₃)₂— | —OC(CH₃)₂C(=O)— | | H | H | H |
| 264 | 1 | —C(CH₃)₂— | —C(=O)C(CH₃)₂O— | | H | H | H |
| 265 | 1 | —C(CH₃)₂— | H | —C(=O)C(CH₃)₂O— | | H | H |
| 266 | 1 | —S— | H | H | Cl | H | H |
| 267 | 1 | —S(O)— | H | H | Cl | H | H |
| 268 | 1 | —S(O)₂— | H | H | Cl | H | H |
| 269 | 1 | —S(O)₂— | H | —CH=CHCH=CH— | | H | H |

Insecticide Formulations

In the normal use of the insecticidal tetrahydroquinazolines of the present invention, they usually will not be employed free from admixture or dilution, but ordinarily will be used in a suitable formulated composition compatible with the method of application and comprising an insecticidally effective amount of the tetrahydroquinazoline. The tetrahydroquinazolines of this invention, like most pesticidal agents, may be blended with the agriculturally acceptable surface-active agents and carriers normally employed for facilitating the dispersion of active ingredients, recognizing the accepted fact that the formulation and mode of application of an insecticide may affect the activity of the material. The present tetrahydroquinazolines may be applied, for example, as sprays, dusts, or granules to the area where pest control is desired, the type of application varying of course with the pest and the environment. Thus, the tetrahydroquinazolines of this invention may be formulated as granules of large particle size, as powdery dusts, as wettable powders, as emulsifiable concentrates, as solutions, and the like. It will be understood that the insecticides themselves may be present as essentially pure compounds, or as mixtures of these tetrahydroquinazoline compounds.

Granules may comprise porous or nonporous particles, such as attapulgite clay or sand, for example, which serve as carriers for the quinazolines. The granule particles are relatively large, a diameter of about 400–2500 microns typically. The particles are either impregnated with the tetrahydroquinazoline from solution or coated with the tetrahydroquinazoline, adhesive sometimes being employed. Granules generally contain 0.05–10%, preferably 0.5–5%, active ingredient as the insecticidally effective amount.

Dusts are admixtures of the tetrahydroquinazolines with finely divided solids such as talc, attapulgite clay, kieselguhr, pyrophyllite, chalk, diatomaceous earths, calcium phosphates, calcium and magnesium carbonates, sulfur, flours, and other organic and inorganic solids which acts carriers for the insecticide. These finely divided solids have an average particle size of less than about 50 microns.

A typical dust formulation useful for controlling insects contains 1 part of Compound 53 and 99 parts of talc.

The tetrahydroquinazolines of the present invention may be made into liquid concentrates by dissolution or emulsification in suitable liquids and into solid concentrates by admixture with talc, clays, and other known solid carriers used in the pesticide art. The concentrates are compositions containing, as an insecticidally effective amount, about 5–50% tetrahydroquinazoline, and 95–50% inert material, which includes surface-active dispersing, emulsifying, and wetting agents, but even higher concentrations of active ingredient may be employed experimentally. The concentrates are diluted with water or other liquids for practical application as sprays, or with additional solid carrier for use as dusts.

By way of illustration, compound 53 is formulated as a 10% wettable powder (10% WP) as follows:

| COMPONENT | AMOUNT (wt/wt) |
|---|---|
| Compound 53 | 10.1% |
| Wetting Agent | 5.0% |
| Dispersing Agent | 3.8% |
| Wetting/Dispersing Agent | 0.9% |
| Diluent | 80.2% |

Manufacturing concentrates are useful for shipping low melting products of this invention. Such concentrates are prepared by melting the low melting solid products together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the tetrahydroquinazolines with a liquid or solid emulsifying agent, or they may also contain a liquid carrier such as xylene, heavy aromatic naphthas, isophorone and other relatively non-volatile organic solvents. For application, these concentrates are dispersed in water or other liquid carriers and normally applied as sprays to areas to be treated.

Typical surface-active wetting, dispersing, and emulsifying agents used in pesticidal formulations include, for example, the alkyl and alkylaryl sulfonates and sulfates and their sodium salts, including fatty methyl taurides; alkylaryl polyether alcohols; sulfates of higher alcohols; polyvinyl alcohols; polyethylene oxides; sulfonated animal and Vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 1–15% by weight of the insecticidal composition.

Other useful formulations include simple solutions of the active ingredient in a solvent in which it is completely soluble at the desired concentrations, such as acetone or other organic solvents.

As shown in the biological test methods below, the compounds of the present invention were tested in the laboratory as dimethyl sulfoxide solutions incorporated into an artificial insect diet or as aqueous acetone or methanol solutions containing a small amount of octylphenoxypolyethoxyethanol surfactant for use as foliar sprays. An insecticidally effective amount of tetrahydroquinazoline in an insecticidal composition diluted for application is normally in the range of about 0.001% to about 8% by weight. Many variations of spraying and dusting compositions known in the art may be used by substituting the tetrahydroquinazoline of this invention into compositions known or apparent in the art.

The insecticidal compositions of this invention may be formulated with other active ingredients, including other insecticides, nematicides, acaricides, fungicides, plant growth regulators, fertilizers, etc.

In using the compositions to control insects, it is only necessary that an insecticidally effective amount of tetrahydroquinazoline be applied to the locus where control is desired. Such locus may, e.g., be the insects themselves, plants upon which the insects feed, or the insect habitat. When the locus is the soil, e.g., soil in which agricultural crops are or will be planted, the active compound may be applied to and optionally incorporated into the soil. For most applications, an insecticidally effective amount will be about 75 to 4000 g per hectare, preferably 150 g to 3000 g per hectare.

Biological Data

The substituted 2,4-diaminotetrahydroquinazoline of the present invention were incorporated into an artificial diet for evaluation of insecticidal activity against the tobacco budworm (*Heliothis virescens* [Fabricius]).

Stock solutions of test chemical in dimethyl sulfoxide were prepared for each rate of application. The rates of application, expressed as the negative log of the molar concentration, and the corresponding concentrations of the stock solution prepared for each rate are shown below:

| Stock Solution | Rate of Application |
|---|---|
| 50 micromolar | 4 |
| 5 | 5 |
| 0.5 | 6 |
| 0.05 | 7 |
| 0.005 | 8 |

One hundred microliters of each of the stock solutions was manually stirred into 50 mL of a molten (65°–70° C.) wheat germ-based artificial diet. The 50 mL of molten diet containing the test chemical was poured evenly into twenty wells in the outer four rows of a twenty-five well, five row plastic tray. Each well in the tray was about 1 cm in depth, with an opening of 3 cm by 4 cm at the lip. Molten diet containing only dimethyl sulfoxide at the levels used in the test chemical-treated diet was poured into the five wells in the third row of the tray. Each tray therefore contained one test chemical at a single rate of application, together with an untreated control.

Single second instar tobacco budworm larvae were placed in each well. The larvae were selected at a stage of growth at which they uniformly weigh about 5 mg each. Upon completion of infestation, a sheet of clear plastic was heat-sealed over the top of the tray using a common household flat iron. The trays were held at 25° C. at 60% relative humidity for five days in a growth chamber. Lighting was set at 14 hours of light and 10 hours of darkness.

After the 5-day exposure period, mortality counts were taken, and the surviving insects were weighed. From the weights of the surviving insects that fed on the treated diet as compared to those insects that fed on the untreated diet, the percent growth inhibition caused by each test chemical was determined. From these data, the negative log of the concentration of the test chemical that provided 50% growth inhibition ($pI_{50}$) was determined by linear regression, when possible, for each test chemical. Where possible, the negative log of the concentration of the test chemical that provided 50% mortality ($pLC_{50}$) was also determined.

The results of the above diet test, as reported in Table 2, below, show that Compounds 4, 7, 53, 59, 266, and 269 of Table 1 all have $pLC_{50}$ values of 5.1 or higher. Compounds 4 and 53 have $pLC_{50}$ values of 5.8, demonstrating their high insecticidal activity.

TABLE 2

Insecticidal Activity of Selected 2,4-Diamino-5,6,7,8-Quinazolines Incorporated into the Diet of Tobacco Budworm

| Cmpd. No. | Rate of Application[1] | Percent Growth Inhibition[2,3,4] | $pI_{50}$[5] | Percent Mortality[6] | $pLC_{50}$[7] |
|---|---|---|---|---|---|
| 1 | 4 | −10 | — | 0 | — |
| 3 | 5 | 4 | 4.0 | 0 | — |
|   | 4 | 52 |   | 0 |   |
| 4 | 7 | −5 | 5.8 | 0 | <4.0 |
|   | 6 | 38 |   | 0 |   |
|   | 5 | 88 |   | 5 |   |
|   | 4 | 96 |   | 30 |   |
| 5 | 4 | 6 | — | 0 | — |
| 6 | 6 | −2 | — | 0 | — |
|   | 5 | 42 |   | 0 |   |
|   | 4 | 88 |   | 15 |   |
| 7 | 8 | — | 5.1 | 0 | — |
|   | 7 | −13 |   | 0 |   |
|   | 6 | 4 |   | 0 |   |
|   | 5 | 67 |   | 0 |   |
|   | 4 | 86 |   | 5 |   |
| 9 | 5 | −4 | <4.0 | 0 | — |
|   | 4 | 33 |   | 5 |   |
| 52 | 6 | −3 | 4.9 | 0 | <4.0 |
|   | 5 | 53 |   | 0 |   |
|   | 4 | 91 |   | 35 |   |
| 53 | 7 | −5 | 5.8 | 0 | <4.0 |
|   | 6 | 43 |   | 0 |   |
|   | 5 | 85 |   | 10 |   |
|   | 4 | 94 |   | 25 |   |
|   | 7 | −6 | 5.5 | 0 | — |
|   | 6 | 16 |   | 0 |   |
|   | 5 | 80 |   | 0 |   |
|   | 4 | 94 |   | 0 |   |
| 59 | 6 | 76 | — | 0 | — |
|   | 5 | 76 |   | 10 |   |
|   | 4 | 94 |   | 15 |   |
|   | 7 | 8 | 5.5 | 0 | <4.0 |
|   | 6 | 25 |   | 0 |   |
|   | 5 | 78 |   | 15 |   |
|   | 4 | 93 |   | 25 |   |
| 257 | 7 | 11 | 5.4 | 0 | <4.0 |
|   | 6 | 21 |   | 0 |   |
|   | 5 | 67 |   | 0 |   |
|   | 4 | 91 |   | 25 |   |
| 266 | 7 | 11 | 5.4 | 0 | <4.0 |
|   | 6 | 21 |   | 0 |   |
|   | 5 | 67 |   | 0 |   |
|   | 4 | 91 |   | 25 |   |
| 269 | 8 | — | 5.1 | 0 | — |
|   | 7 | −13 |   | 0 |   |
|   | 6 | 4 |   | 0 |   |

TABLE 2-continued

Insecticidal Activity of Selected 2,4-Diamino-5,6,7,8-Quinazolines Incorporated into the Diet of Tobacco Budworm

| Cmpd. No. | Rate of Application[1] | Percent Growth Inhibition[2,3,4] | $pI_{50}$[5] | Percent Mortality[6] | $pLC_{50}$[7] |
|---|---|---|---|---|---|
|   | 5 | 67 |   | 0 |   |
|   | 4 | 86 |   | 5 |   |

FOOTNOTES

[1] The rate of application is expressed as the negative log of the molar concentration of the test compound in the diet.
[2] Percent growth inhibition is derived from the total weight of the insects (IW) at each rate of application in the test relative to the total weight of insects in an untreated control,
% Gr. Inh. = [IW (control) − IW (test) / IW (control)] × 100
[3] ND = No data
[4] A minus % growth inhibition indicates that the insects weighed more at the termination of the test than those in the untreated control.
[5] $pI_{50}$ is the negative log of the concentration of the test chemical that provides 50% growth inhibition in the test insects.
[6] Percent mortality is derived from the total number of dead insects (TD) relative to the total number of insects (TI) used in the test,
% Mortality = $\frac{TD}{TI}$ × 100
[7] $pLC_{50}$ is the negative log of the concentration of the test chemical that provides 50% mortality of the test insects.

We claim:

1. An insecticidal composition comprising, in admixture with an agriculturally acceptable carrier, and a surface-active agent other than is used in pharmaceutical formulations, an insecticidally effective amount of a tetrahydroquinazoline compound of the formula wherein R and $R^1$ are amino;

$R^2$, $R^3$, $R^5$, $R^6$, $R^7$, $R^8$, and $R^9$ are hydrogen; and $R^4$ is lower alkyl.

2. The composition of claim 1 wherein the tetrahydroquinazoline is 2,4-diamino-6-(1,1-dimethylethyl)-5,6,7,8-tetrahydroquinazoline.

3. A method for controlling insects which comprises applying to the locus where control is desired an insecticidal amount of the composition of claim 1.

* * * * *